(12) United States Patent
Linehan et al.

(10) Patent No.: US 6,312,890 B1
(45) Date of Patent: *Nov. 6, 2001

(54) PARTIAL INTRON SEQUENCE OF VON HIPPEL-LINDAU (VHL) DISEASE GENE AND ITS USE IN DIAGNOSIS OF DISEASE

(75) Inventors: W. Marston Linehan; Michael I. Lerman, both of Rockville, MD (US); Farida Latif, Birmingham (GB); Berton Zbar, Garrett Park, MD (US)

(73) Assignee: The United States of America as represented by the Department of Health and Human Services, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/623,428

(22) Filed: Mar. 28, 1996

Related U.S. Application Data

(63) Continuation-in-part of application No. 08/061,889, filed on May 14, 1993, now Pat. No. 5,654,138.

(51) Int. Cl.$^7$ .............................. C12Q 1/68; C12P 19/34; C07H 21/04
(52) U.S. Cl. ........................... 435/6; 435/91.2; 536/23.1; 536/23.5; 536/24.31; 536/24.33
(58) Field of Search .................... 435/6, 91.2; 536/23.1, 536/24.31, 24.33, 23.5

(56) References Cited

PUBLICATIONS

Sekido et al. Oncogene. 9:1599–1604, 1994.*

* cited by examiner

*Primary Examiner*—Carla J. Myers
(74) *Attorney, Agent, or Firm*—Morgan & Finnegan LLP

(57) ABSTRACT

The Von Hippel-Lindau (VHL) disease gene and its corresponding cDNA are disclosed. Methods for detecting carriers of the VHL disease gene using probes derived from the VHL disease gene sequence are described. Pharmaceutical compositions and methods of treating diseases related to the VHL gene are also disclosed.

24 Claims, 19 Drawing Sheets

FIG. 3B
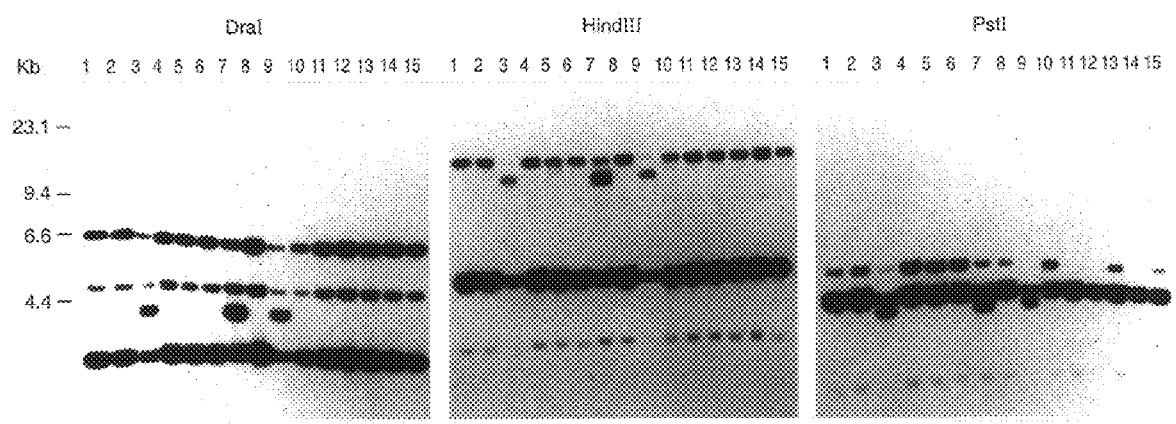
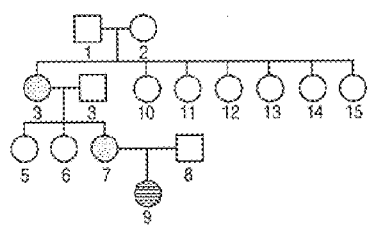
FIG. 3C

```
                                                                SP1
-468    AGAGGCCAAG  GCAGGAGGAT  CACTTGAACC  CAGGAGTTCG
-428    AGACCAGCCT  AGGCAACATA  GCGAGACTCC  GTTTCAAACA
               term                                      BssHII
-388    ACAAATAAAA  ATAATTAGTC  GGGCATGGTG  GTGCGCGCCT
                                       SP1
-348    ACAGTACCAA  CTACTCGGGA  GGCTGAGGCG  AGACGATCGC -308    TTGAGCCAGG  GAGGTCAAGG  CTGCAGTGAG  CCAAGCTCGC
                          SmaI AP-2                  Tth 111 I
-268    GCCACTGCAC  TCCAGCCCGG  GCGACAGAGT  GAGACCCTGT

-228    CTCCAAAAAA  AAAAAAAAAC  ACCAAACCTT  AGAGGGGTGA

-188    AAAAAAATTT  TATAGTGGAA  ATACAGTAAC  GAGTTGGCCT

-148    AGCCTCGCCT  CCGTTACAAC  AGCCTACGGT  GCTGGAGGAT
                                        EagI
-108    CCTTCTGCGC  ACGCGCACAG  CCTCCGGCCG  GCTATTTCCG
                                        BssHII BssHII
 -68    CGAGCGCGTT  CCATCCTCTA  CCGAGCGCGC  GCGAAGACTA
            SalI             BssHII      +1  SP1/AP2
 -28    CGGAGGTCGA  CTCGGGAGCG  CGCACGCAGC  TCCGCCCCGC
            SacII        SacII           SmaI
 +13    GTCCGACCCG  CGGATCCCGC  GGCGTCCGGC  CCGGGTGGTC
                                        SP1/AP2
 +53    TGGATCGCGG  AGGGAATGCC  CCGGAGGGCG  GAGAACTGGG

+93    ACGAGGCCGA  GGTAGGCGCG  GAGGAGGCAG  GCGTCGAAGA
                                                NarI
+133    GTACGGCCCT  GAAGAAGACG  GCGGGGAGGA  GTCGGGCGCC

+173    GAGGAGTCCG  GCCCGGAAGA  GTC
```

FIG. 12

Exon 1
5'
TACCCAACGCTGCCGCCCTGGCACGGGCCGCATCCACAGCTACCGAGgtac
gggcccgcggcgcttaggcccgacccagagcaggacgatagcacggtctaagcccctctaccgccccggggtccattcagacggg
gaactaggccccttgaggcaggacacatccaggt Exon 2
5'
ctcctgacctctatgatccgcctgcctccggctccggcctccaaagtgctgggattacaggtgtgggccaccgtgcccagccaccggtGT
GGCTCtttaacaacctttgcttgtcccgatagGTCACCTTTGGCTCTTCAGAGATGCAGGAC
ACACGATGGGCTTCTGGTTAACCAAACTGAATTATCACACTGCCATCTCTCAAT
GTTGACGGACAGCCTATTTTTGCCAATATCACACTGCCAGtactgacgttttactttttaa
aagataaggttgttgtggtacaggatagaccacttgaagccagttctcaattttgcctgatgtgtcaggcacggt
atccaatcttttttgtatcctattctctaccataaaataaaatgaagtgatgatttt Exon 3
5'
ctacagaaggcatgaacaccatgaagtgtccataggggccacagcatacacactgccacatacatgcactcacttttttctttaa
cctaaaagtgaagatccatcagtagtacaggtagttggcaaaagcctcttgttccttgtactgagacccctagtctgccact
gaggatttggttttgccc

FIG. 13

SEQUENCE LISTING (1) GENERAL INFORMATION:

(iii) NUMBER OF SEQUENCES: 63

(2) INFORMATION FOR SEQ ID NO: 1:

(i) SEQUENCE CHARACTERISTICS:
      (A) LENGTH: 1816 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
CCTCGCCTCC GTTACAACAG CCTACGGTGC TGGAGGATCC                    40

TTCTGCGCAC GCGCACAGCC TCCGGCCGGC TATTTCCGCG                    80

AGCGCGTTCC ATCCTCTACC GAGCGCGCGC GAAGACTACG                   120
```

-continued

| | |
|---|---|
| GAGGTCGACT CGGGAGCGCG CACGCAGCTC CGCCCCGCGT | 160 |
| CCGACCCGCG GATCCCGCGG CGTCCGGCCC GGGTGGTCTG | 200 |
| GATCGCGGAG GGAATGCCCC GGAGGGCGGA GAACTGGGAC | 240 |
| GAGGCCGAGG TAGGCGCGGA GGAGGCAGGC GTCGAAGAGT | 280 |
| ACGGCCCTGA AGAAGACGGC GGGGAGGAGT CGGGCGCCGA | 320 |
| GGAGTCCGGC CCGGAAGAGT CCGGCCCGGA GGAACTGGGC | 360 |
| GCCGAGGAGG AGATGGAGGC CGGGCGGCCG CGGCCCGTGC | 400 |
| TGCGCTCGGT GAACTCGCGC GAGCCCTCCC AGGTCATCTT | 440 |
| CTGCAATCGC AGTCCGCGCG TCGTGCTGCC CGTATGGCTC | 480 |
| AACTTCGACG GCGAGCCGCA GCCCTACCCA ACGCTGCCGC | 520 |
| CTGGCACGGG CCGCCGCATC CACAGCTACC GAGGTCACCT | 560 |
| TTGGCTCTTC AGAGATGCAG GGACACACGA TGGGCTTCTG | 600 |
| GTTAACCAAA CTGAATTATT TGTGCCATCT CTCAATGTTG | 640 |
| ACGGACAGCC TATTTTTGCC AATATCACAC TGCCAGTGTA | 680 |
| TACTCTGAAA GAGCGATGCC TCCAGGTTGT CCGGAGCCTA | 720 |
| GTCAAGCCTG AGAATTACAG GAGACTGGAC ATCGTCAGGT | 760 |
| CGCTCTACGA AGATCTGGAA GACCACCCAA ATGTGCAGAA | 800 |
| AGACCTGGAG CGGCTGACAC AGGAGCGCAT TGCACATCAA | 840 |
| CGGATGGGAG ATTGAAGATT TCTGTTGAAA CTTACACTGT | 880 |
| TTCATCTCAG CTTTTGATGG TACTGATGAG TCTTGATCTA | 920 |
| GATACAGGAC TGGTTCCTTC CTTAGTTTCA AAGTGTCTCA | 960 |
| TTCTCAGAGT AAAATAGGCA CCATTGCTTA AAAGAAAGTT | 1000 |
| AACTGACTTC ACTAGGCATT GTGATGTTTA GGGGCAAACA | 1040 |
| TCACAAAATG TAATTTAATG CCTGCCCATT AGAGAAGTAT | 1080 |
| TTATCAGGAG AAGGTGGTGG CATTTTTGCT TCCTAGTAAG | 1120 |
| TCAGGACAGC TTGTATGTAA GGAGGTTTAT ATAAGTAATT | 1160 |
| CAGTGGGAAT TGCAGCATAT CGTTTAATTT TAAGAAGGCA | 1200 |
| TTGGCATCTG CTTTTAATGG ATGTATAATA CATCCATTCT | 1240 |
| ACATCCGTAG CGGTTGGTGA CTTGTCTGCC TCCTGCTTTG | 1280 |
| GGAAGACTGA GGCATCCGTG AGGCAGGGAC AAGTCTTTCT | 1320 |
| CCTCTTTGAG ACCCCAGTGC CTGCACATCA TGAGCCTTCA | 1360 |
| GTCAGGGTTT CTCAGAGGAA CAAACCAGGG GACACTTTGT | 1400 |
| TAGAAAGTGC TTAGAGGTTC TGCCTCTATT TTTGTTGGGG | 1440 |
| GGTGGGAGAG GGGACCTTAA AATGTGTACA GTGAACAAAT | 1480 |
| GTCTTAAAGG GAATCATTTT TGTAGGAAGC ATTTTTTATA | 1520 |
| ATTTTCTAAG TCGTGCACTT TCTCGGTCCA CTCTTGTTGA | 1560 |
| AGTGCTGTTT TATTACTGTT TCTAAACTAG GATTGACATT | 1600 |
| CTACAGTTGT GATAATAGCA TTTTTGTAAC TTGCCATCCG | 1640 |
| CACAGAAAAT ACGAGAAAAT CTGCATGTTT GATTATAGTA | 1680 |

```
TTAATGGACA AATAAGTTTT TGCTAAATGT GAGTATTTCT                              1720

GTTCCTTTTT GTAAATATGT GACATTCCTG ATTGATTTGG                              1760

GTTTTTTTGT TGTTGTTGTT TTGTTTTGTT TTGTTTTTTT                              1800

GGGATGGAGG GAATTC                                                        1816
```

(2) INFORMATION FOR SEQ ID NO: 2:

(i) SEQUENCE CHARACTERISTICS:
        (A) LENGTH: 284 amino acids
        (B) TYPE: amino acid
        (C) STRANDEDNESS: single
        (D) TOPOLOGY: linear (xi) SEQUENCE DESCRIPTION: SEQ ID NO: 2:

```
Pro Arg Leu Arg Tyr Asn Ser Leu Arg Cys Trp Arg
                 5                  10

Ile Leu Leu Arg Thr Arg Thr Ala Ser Gly Arg Leu
             15                  20

Phe Pro Arg Ala Arg Ser Ile Leu Tyr Arg Ala Arg
 25                  30                  35

Ala Lys Thr Thr Glu Val Asp Ser Gly Ala Arg Thr
             40                  45

Gln Leu Arg Pro Ala Ser Asp Pro Arg Ile Pro Arg
 50                  55                  60

Arg Pro Ala Arg Val Val Trp Ile Ala Glu Gly Met
             65                  70

Pro Arg Arg Ala Glu Asn Trp Asp Glu Ala Glu Val
             75                  80

Gly Ala Glu Glu Ala Gly Val Glu Glu Tyr Gly Pro
 85                  90                  95

Glu Glu Asp Gly Gly Glu Glu Ser Gly Ala Glu Glu
                100                 105

Ser Gly Pro Glu Glu Ser Gly Pro Glu Glu Leu Gly
         110                 115                 120

Ala Glu Glu Glu Met Glu Ala Gly Arg Pro Arg Pro
                125                 130

Val Leu Arg Ser Val Asn Ser Arg Glu Pro Ser Gln
         135                 140

Val Ile Phe Cys Asn Arg Ser Pro Arg Val Val Leu
145                 150                 155

Pro Val Trp Leu Asn Phe Asp Gly Glu Pro Gln Pro
                160                 165

Tyr Pro Thr Leu Pro Pro Gly Thr Gly Arg Arg Ile
         170                 175                 180

His Ser Tyr Arg Gly His Leu Trp Leu Phe Arg Asp
                185                 190

Ala Gly Thr His Asp Gly Leu Leu Val Asn Gln Thr
         195                 200

Glu Leu Phe Val Pro Ser Leu Asn Val Asp Gly Gln
205                 210                 215

Pro Ile Phe Ala Asn Ile Thr Leu Pro Val Tyr Thr
                220                 225

Leu Lys Glu Arg Cys Leu Gln Val Arg Ser Leu
         230                 235                 240
```

```
Val Lys Pro Glu Asn Tyr Arg Arg Leu Asp Ile Val
                245                 250

Arg Ser Leu Tyr Glu Asp Leu Glu Asp His Pro Asn
        255                 260

Val Gln Lys Asp Leu Glu Arg Leu Thr Gln Glu Arg
265                 270                 275

Ile Ala His Gln Arg Met Gly Asp
            280
```

(2) INFORMATION FOR SEQ ID NO: 3:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
TACCCAACGC TGCCGCCTGG CACGGGCCGC CGCATCCACA                40

GCTACCGAGG TACGGGCCCG GCGCTTAGGC CCGACCCAGC                80

AGGACGATAG CACGGTCTAA GCCCCTCTAC CGCCCCGGGG               120

TCCATTCAGA CGGGGAACTA GGCCCCTTGA GGCAGGACAC               160

ATCCAGGGT                                                 169
```

(2) INFORMATION FOR SEQ ID NO: 4:

(i) SEQUENCE CHARACTERISTICS:
        (A) LENGTH: 403 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
CTCCTGACCT CTATGATCCG CCTGCCTCGG CCTCCAAAGT                40

GCTGGGATTA CAGGTGTGGG CCACCGTGCC CAGCCACCGG                80

TGTGGCTCTT TAACAACCTT TGCTTGTCCC GATAGGTCAC               120

CTTTGGCTCT TCAGAGATGC AGGGACACAC GATGGGCTTC               160

TGGTTAACCA AACTGAATTA TTTGTGCCAT CTCTCAATGT               200

TGACGGACAG CCTATTTTTG CCAATATCAC ACTGCCAGGT               240

ACTGACGTTT TACTTTTTAA AAAGATAAGG TTGTTGTGGT               280

AAGTACAGGA TAGACCACTT GAAAAATTAA GCCCAGTTCT               320

CAATTTTTGC CTGATGTCAG GCACGGTATC CAATCTTTTT               360

GTATCCTATT CTCTACCATA AATAAAATGG AAGTGATGAT               400

TTT                                                       403
```

(2) INFORMATION FOR SEQ ID NO: 5:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

| | |
|---|---|
| CTACAGAAGG CATGAACACC ATGAAGTGTC CATAGGGGCC | 40 |
| ACAGCATACA CACTGCCACA TACATGCACT CACTTTTTTT | 80 |
| CTTTAACCTA AAAGTGAAGA TCCATCAGTA GTACAGGTAG | 120 |
| TTGTTGGCAA AAGCCTCTTG TTCGTTCCTT GTACTGAGAC | 160 |
| CCTAGTCTGC CACTGAGGAT TTGGTTTTTG CCC | 193 |

(2) INFORMATION FOR SEQ ID NO: 6:

(i) SEQUENCE CHARACTERISTICS:
        (A) LENGTH: 663 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

| | |
|---|---|
| AGAGGCCAAG GCAGGAGGAT CACTTGAACC CAGGAGTTCG | 40 |
| AGACCAGCCT AGGCAACATA GCGAGACTCC GTTTCAAACA | 80 |
| ACAAATAAAA ATAATTAGTC GGGCATGGTG GTGCGCGCCT | 120 |
| ACAGTACCAA CTACTCGGGA GGCTGAGGCG AGACGATCGC | 160 |
| TTGAGCCAGG GAGGTCAAGG CTGCAGTGAG CCAAGCTCGC | 200 |
| GCCACTGCAC TCCAGCCCGG GCGACAGAGT GAGACCCTGT | 240 |
| CTCCAAAAAA AAAAAAAAAC ACCAAACCTT AGAGGGGTGA | 280 |
| AAAAAAATTT TATAGTGGAA ATACAGTAAC GAGTTGGCCT | 320 |
| AGCCTCGCCT CCGTTACAAC AGCCTACGGT GCTGGAGGAT | 360 |
| CCTTCTGCGC ACGCGCACAG CCTCCGGCCG GCTATTTCCG | 400 |
| CGAGCGCGTT CCATCCTCTA CCGAGCGCGC GCGAAGACTA | 440 |
| CGGAGGTCGA CTCGGGAGCG CGCACGCAGC TCCGCCCCGC | 480 |
| GTCCGACCCG CGGATCCCGC GGCGTCCGGC CCGGGTGGTC | 520 |
| TGGATCGCGG AGGGAATGCC CCGGAGGGCG GAGAACTGGG | 560 |
| ACGAGGCCGA GGTAGGCGCG GAGGAGGCAG GCGTCGAAGA | 600 |
| GTACGGCCCT GAAGAAGACG GCGGGGAGGA GTCGGGCGCC | 640 |
| GAGGAGTCCG GCCCGGAAGA GTC | 663 |

(2) INFORMATION FOR SEQ ID NO: 7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

| | |
|---|---|
| ATAGTGGAAA TACAGTAACG AGTTGGCCTA GCCTCGC | 37 |

(2) INFORMATION FOR SEQ ID NO: 8:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 8:

CCCAGCTGGG TCGGGCCTAA GCGCCGGGCC CGT                33

(2) INFORMATION FOR SEQ ID NO: 9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GTGGCTCTTT AACAACCTTT GCTTGTCCCG ATA                33

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

CAAGTGGTCT ATCCTGTACT TACCACAACA CCT                33

(2) INFORMATION FOR SEQ ID NO: 11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

TGTATACTCT GAAAGAGCGA TGCCTCCAGG T                  31

(2) INFORMATION FOR SEQ ID NO: 12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

TACCATCAAA AGCTGAGATG AAACAGTGTA AGT                33

(2) INFORMATION FOR SEQ ID NO: 13:

(i) SEQUENCE CHARACTERISTICS:
        (A) LENGTH: 27 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO: 13:

AGTGGAAATA CAGTAACGAG TTGGCCT                                              27

(2) INFORMATION FOR SEQ ID NO: 14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

GAAATACAGT AACGAGTTGG CCTAGC                                               26

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

GTCCCAGTTC TCCGCCCTCC GGGGCAT                                              27

(2) INFORMATION FOR SEQ ID NO: 16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

TGGGTCGGGC CTAAGCGCCG GGCCCGT                                              27

(2) INFORMATION FOR SEQ ID NO: 17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

CTTTAACAAC CTTTGCTTGT CCCGATA                                              27

(2) INFORMATION FOR SEQ ID NO: 18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

GTGGCTCTTT AACAACCTTG C                                              21

(2) INFORMATION FOR SEQ ID NO: 19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

GTCTATCCTG TACTTACCAC AACACCT                                        27

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

CCTGTACTTA CCACAACACC TTAT                                           24

(2) INFORMATION FOR SEQ ID NO: 21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

CTGAGACCCT AGTCTGCCAC TGAGGAT                                        27

(2) INFORMATION FOR SEQ ID NO: 22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

TTCCTTGTAC TGAGACCCTA GT                                             22

(2) INFORMATION FOR SEQ ID NO: 23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

GGAAATACAG TAACGAGTTG GCCT                                           24

(2) INFORMATION FOR SEQ ID NO: 24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

GGAAATACAG TAACGAGTTG GCCTAGC                               27

(2) INFORMATION FOR SEQ ID NO: 25:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

ACGGGCCCGG CGCTTAGGCC CGACCCA                               27

(2) INFORMATION FOR SEQ ID NO: 26:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

ACGGGCCCGG CGCTTAGGCC CGACCCAGCA GG                         32

(2) INFORMATION FOR SEQ ID NO: 27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

GTGGCTCTTT AACAACCTTT GCTTGTCCCG ATA                        33

(2) INFORMATION FOR SEQ ID NO: 28:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

CTTTAACAAC CTTTGC                                                  16

(2) INFORMATION FOR SEQ ID NO: 29:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

GATAAGGTTG TTGTGGTAAG TACAGGA                                    27

(2) INFORMATION FOR SEQ ID NO: 30:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

AGGTTGTTGT GGTAAGTACA GGATAGC                                    27

(2) INFORMATION FOR SEQ ID NO: 31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

CTCCTTGTAC TGAGACCCTA GT                                         22

(2) INFORMATION FOR SEQ ID NO: 32:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

GTGAGACCCT AGTCTGCCAC TGAGGAT                                    27

(2) INFORMATION FOR SEQ ID NO: 33:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

GAGGTCAC                                                          8

(2) INFORMATION FOR SEQ ID NO: 34:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 34:

GATTGGTCAC                                                           10

(2) INFORMATION FOR SEQ ID NO: 35:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 35:

Glu Glu Tyr Gly Pro Glu Glu Asp Gly Gly Glu Glu
                 5                  10

Ser Gly (2) INFORMATION FOR SEQ ID NO: 36:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO: 36:

Gly Thr Gly Arg Arg Ile His Ser Tyr Arg Gly His
                 5                  10

Leu (2) INFORMATION FOR SEQ ID NO: 37:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

ACGACGCGCG GACTGCGATT GCAGAAGAT                                      29

(2) INFORMATION FOR SEQ ID NO: 38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:

AGCGACCTGA CGATGTCCAG TCTC                                           24

(2) INFORMATION FOR SEQ ID NO: 39:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

CCTCGCCTCC GTTACAACA                                                                19

(2) INFORMATION FOR SEQ ID NO: 40:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

GGATCCTAAT ACGACTCACT ATAGGGAGGC GCCCGACTCC                                         40

TCCC                                                                                44

(2) INFORMATION FOR SEQ ID NO: 41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 41:

CTATCTAGAG GCCAAGGCAG GAGGATC                                                       27

(2) INFORMATION FOR SEQ ID NO: 42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 42:

CATTCTAGAT TCCCTCCGCG ATCCAGA                                                       27

(2) INFORMATION FOR SEQ ID NO: 43:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 43:

CATTCTAGAC TCTTCCGGGC CGGACTC                                                       27

(2) INFORMATION FOR SEQ ID NO: 44:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 44:

CACAAGTGAT GCCTTGTAGC TG                                                            22

(2) INFORMATION FOR SEQ ID NO: 45:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 45:

CAGTAGTGTC CTGTATTTAG TG                                    22

(2) INFORMATION FOR SEQ ID NO: 46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

GTTGGCTATG GGTAGAATTG G                                     21

(2) INFORMATION FOR SEQ ID NO: 47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 47:

CAGGGTAGCC TTGATCTAAG T                                     21

(2) INFORMATION FOR SEQ ID NO: 48:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 48:

GGAGGTCCTG AGAATATGTG TCC                                 23

(2) INFORMATION FOR SEQ ID NO: 49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 49:

TGTTCAGGCA CACAGTAGAT G                                     21

(2) INFORMATION FOR SEQ ID NO: 50:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 50:

CATCTTCTGC AATCGCAGTC CGCGCGT                               27

(2) INFORMATION FOR SEQ ID NO: 51:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 51:

CAAAAGCTGA GATGAAACAG TGTAAGT                               27

(2) INFORMATION FOR SEQ ID NO: 52:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 52:

GTTTGGTTAA CCAGAAGCCC ATCGT                                 25

(2) INFORMATION FOR SEQ ID NO: 53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 53:

GATGGGCTTC TGGTTAACCA AACT                                  24

(2) INFORMATION FOR SEQ ID NO: 54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 54:

GGTCCAACAG GCCTCGGA                                         18

(2) INFORMATION FOR SEQ ID NO: 55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 55:

AGGCCAACAG GCATCGGA                                                         18

(2) INFORMATION FOR SEQ ID NO: 56

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 56

KRGGCGKRRY                                                                  10

(2) INFORMATION FOR SEQ ID NO: 57

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO: 57

YGCGCAYGGC R                                                                11

(2) INFORMATION FOR SEQ ID NO: 58

(i) SEQUENCE CHARACTERISTICS:
        (A) LENGTH: 4 base pairs
        (B) TYPE: nucleic acid
        (C) STRANDEDNESS: single
        (D) TOPOLOGY: linear (xi) SEQUENCE DESCRIPTION: SEQ ID NO: 58

TATA                                                                         4

(2) INFORMATION FOR SEQ ID NO: 59

(i) SEQUENCE CHARACTERISTICS:
        (A) LENGTH: 5 base pairs
        (B) TYPE: nucleic acid
        (C) STRANDEDNESS: single
        (D) TOPOLOGY: linear (xi) SEQUENCE DESCRIPTION: SEQ ID NO: 59

CCAAT                                                                        5

(2) INFORMATION FOR SEQ ID NO: 60

(i) SEQUENCE CHARACTERISTICS:
        (A) LENGTH: 9 base pairs
        (B) TYPE: nucleic acid
        (C) STRANDEDNESS: single
        (D) TOPOLOGY: linear (xi) SEQUENCE DESCRIPTION: SEQ ID NO: 60

YCSCCMNSS                                                                    9

(2) INFORMATION FOR SEQ ID NO: 61

(i) SEQUENCE CHARACTERISTICS:
        (A) LENGTH: 9 base pairs
        (B) TYPE: nucleic acid
        (C) STRANDEDNESS: single
        (D) TOPOLOGY: linear (xi) SEQUENCE DESCRIPTION: SEQ ID NO: 61

-continued

```
KRGGCKRRK                                                              9

(2) INFORMATION FOR SEQ ID NO: 62

(i) SEQUENCE CHARACTERISTICS:
        (A) LENGTH: 5 base pairs
        (B) TYPE: nucleic acid
        (C) STRANDEDNESS: single
        (D) TOPOLOGY: linear (xi) SEQUENCE DESCRIPTION: SEQ ID NO: 62

GTTCC                                                                  5

(2) INFORMATION FOR SEQ ID NO: 63

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO: 63

GAGCTC                                                                 6
```

PARTIAL INTRON SEQUENCE OF VON HIPPEL-LINDAU (VHL) DISEASE GENE AND ITS USE IN DIAGNOSIS OF DISEASE

This application is a continuation-in-part of Ser. No. 08/061,889, May 14, 1993, now U.S. Pat. No. 5,654,138.

FIELD OF THE INVENTION

The invention is in the field of tumor suppressor genes. More specifically, the invention relates to the Von Hippel-Lindau (VHL) disease gene and its corresponding cDNA and to methods for detecting carriers of the VHL disease gene using probes derived from the DNA sequences of the present invention.

BACKGROUND OF THE INVENTION

Von Hippel-Lindau (VHL) disease is a familial cancer syndrome. This disease is an autosomal dominant disorder and patients who are heterozygous for mutations in the VHL disease gene are predisposed to a variety of cancers, the most frequent being hemangioblastomas of the central nervous system and retina, renal cell carcinoma (RCC) and pheochromocytoma. The multisystem character of the illness, combined with the fact multiple tumors may form in each target organ, produces considerable morbidity and mortality as evidenced by the reduction in life expectancy of affected individuals to 49 years (McKusick, V. A., Mendelian Inheritance in Man (1983) Johns Hopkins University Press, Baltimore and London, p 534–535). Although the prevalence of VHL disease is only 1 in 36,000, because of its late onset most individuals have children before they realize they have inherited VHL disease. For many years, the only method of presymptomatic or prenatal diagnosis of the disease has been periodic examination of the eye, brain, and abdomen in all asymptomatic members of VHL families. Unfortunately, examination of all target organs is required to ensure detection of disease that may be limited to a single organ. In addition to the obvious inconvenience and the cost of these examinations, they have the additional drawback that they may not yield definitive diagnostic information. Therefore, in order to develop a method which allows the unequivocal diagnosis of VHL disease in individuals at risk, researchers have focused intensive efforts on identifying and isolating the VHL disease gene.

Results of this research have shown that the VHL disease gene is a member of the family of tumor suppressor genes (Tory, K. et al. J. Natl. Canc. Inst. (1989) 81:1097–1101; Maher, E. R. et al. J. Med. Genet. (1990) 27:311–314) and that it behaves in accordance with Knudson's theory of human carcinogenesis (Knudson, A., Proc. Natl. Acad Sci. USA (1971) 68:816–823). In addition, the identification of DNA markers tightly linked to the VHL disease gene has allowed localization of the VHL disease gene to human chromosome 3p25-p26. (Hosoe, S. et al. Genomics (1990) 8:634–640; Maher, E. R. et al. Genomics (1990) 8:957–960; Glenn, G. M. et al. Hum. Genet. (1990) 87: 207–210, Latif, F. et al. Am J. Hum. Genet. (1992) 51 (suppl.) A63; Tory, K. et al. Genomics (1992) 13:275–286; Richards, F. M. et al. J. Med. Genet. (1993) 30:104–107); Seizinger, B. R. et al. Nature (1988) 332:268–269; Seizinger, B. R. et al. Proc. Natl. Acad. Sci. USA (1991) 88:2864–2868 and Vance J. M. et al. Am J. Hum. Genet. (1993) 51:203–209)). Recently, Glenn et al. (Glenn, G. M. et al. JAMA (1992) 1226–1231) have used DNA markers flanking the VHL disease gene as probes to detect linkage to the VHL disease gene via restriction fragment polymorphism analysis of DNA isolated from individuals who are members of families at risk for VHL disease. Although this DNA polymorphism method results in enhanced accuracy of identification of carriers of VHL disease gene, the method is inherently flawed in that DNA polymorphism analysis does not detect the VHL disease gene itself. More recently, a gene located in the VHL region has been cloned (Latif, F. et al. Cancer Res. (1993) 53:861–867). However, this gene was found to detect no mutation in VHL patients and thus, there are currently no available methods which can identify carriers of the VHL disease gene with 100% accuracy. However, the recent identification and isolation of the VHL disease gene (Latif et al., Science, (1993) 260:1317–1320) and its corresponding cDNA should allow the development of diagnostic methods which provide unequivocal detection of carriers of the VHL disease gene.

SUMMARY OF THE INVENTION

The present invention relates to the von Hippel-Lindau (VHL) disease gene and its corresponding cDNA.

The invention further relates to methods for detecting carriers of the VHL gene. The first method comprises analyzing DNA of a subject for mutations of the VHL disease gene associated with VHL disease or other diseases, including, but not limited to, sporadic renal cancer, lung cancer, uterine cancer, breast cancer, testicular cancer, ovarian cancer, adrenal tumors, brain tumors, lung tumors or other cancers.

The second method comprises analyzing RNA of a subject for mutations or alterations in the VHL-specific mRNA associated with VHL disease or other diseases, including, but not limited to, sporadic renal cancer, lung cancer, uterine cancer, breast cancer, testicular cancer and ovarian cancer.

The third method comprises analyzing protein of a subject for alterations in VHL protein expression associated with VHL disease or other diseases, including, but not limited to, sporadic renal cancer, lung cancer, uterine cancer, breast cancer, testicular cancer and ovarian cancer.

The invention also encompasses recombinant VHL proteins derived from the VHL cDNA and antibodies directed against said VHL proteins or peptides derived therefrom.

The invention further relates to a method for treating a carrier of the VHL gene in which an expression vector containing a nucleic acid sequence representing the wild-type VHL gene is administered to the carrier.

The invention also provides a diagnostic kit for detecting carriers of the VHL gene. The kit comprises purified and isolated nucleic acid sequences useful as PCR primers in analyzing DNA or RNA for mutations of the VHL gene associated with VHL disease and diseases related thereto, including, but not limited to, sporadic renal cancer, lung cancer, uterine cancer, breast cancer, testicular cancer and ovarian cancer.

BRIEF DESCRIPTION OF THE FIGURES

FIG. 1 shows a genetic and physical map of the chromosome 3p region encompassing the VHL gene. Genetic and physical distances between selected markers are shown in centiMorgans and kilobases, respectively. The location of selected cross-overs is indicated by crosses. Panel B shows the 160 kb cosmid and phage contig covering the VHL region. An enlarged restriction map of cos3, cos11, and phage p191 detailing the position of g7 cDNA isolated by screening a λgt11 teratocarcinoma cDNA library with a conserved 7 kb fragment from the centromeric end of cosIl.

The beginning of the smallest constitutional deletion is indicated by an asterisk and line. Restriction sites: B, Bam HI; E, Eco RI; N, Not I; Nr, Nru I; M, Mlu I.

Figure 2A:
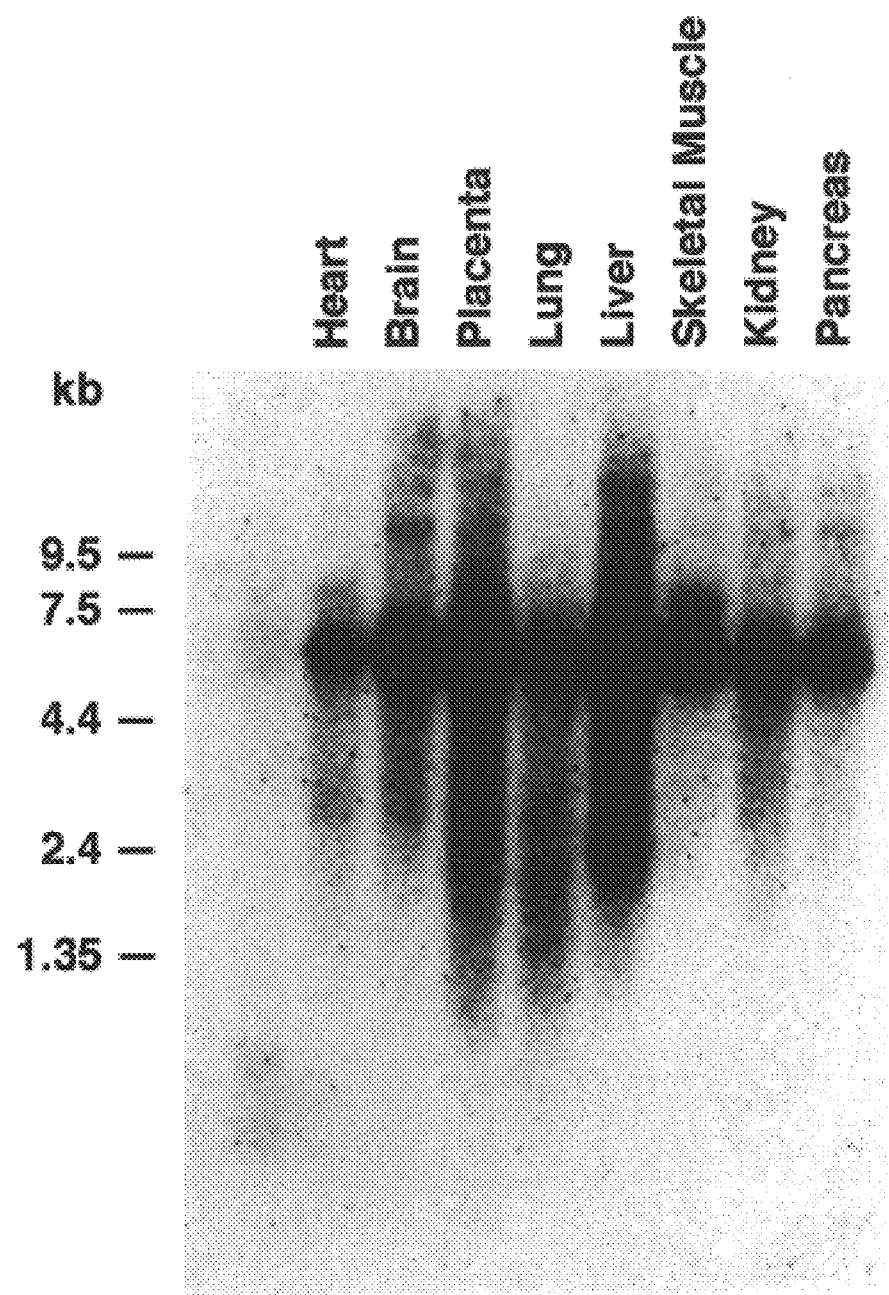
Figure 2B:
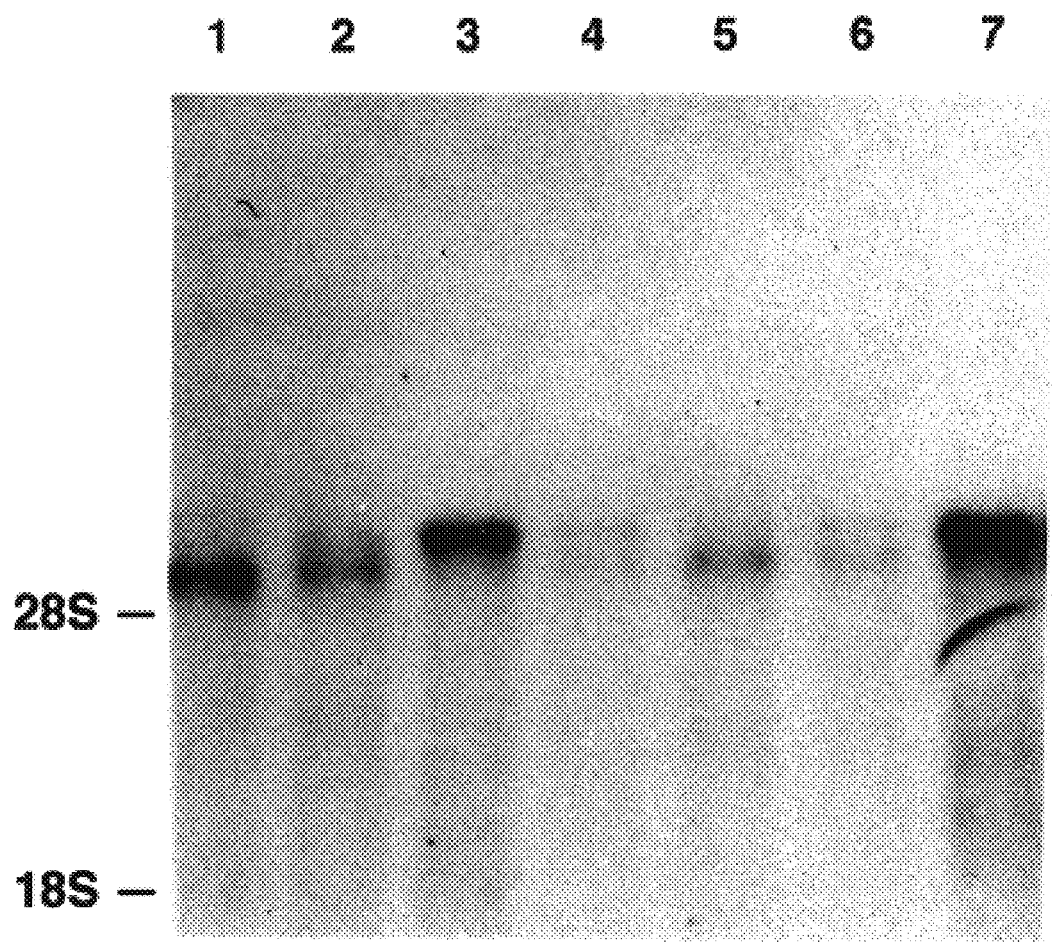

FIGS. 2A and 2B: FIGS. 2A and 2B set forth a Northern blot analysis of the expression of the VHL gene represented by g7 cDNA in various human tissues. FIG. 2A shows a low resolution blot containing 2 µg poly A+ mRNA. The tissues are indicated above the lanes. FIG. 2B shows a high resolution blot containing 1 µg of poly A+ mRNA from: lane 1, fetal brain; lane 2, adult brain; lane 3, fetal kidney; lane 4, adult kidney; lane 5, cerebellum; lane 6, adult adrenal; and lane 7, prostate. The sizes of the transcripts were determined by the position of the 28S and 18S rRNA bands.

Figure 3A:
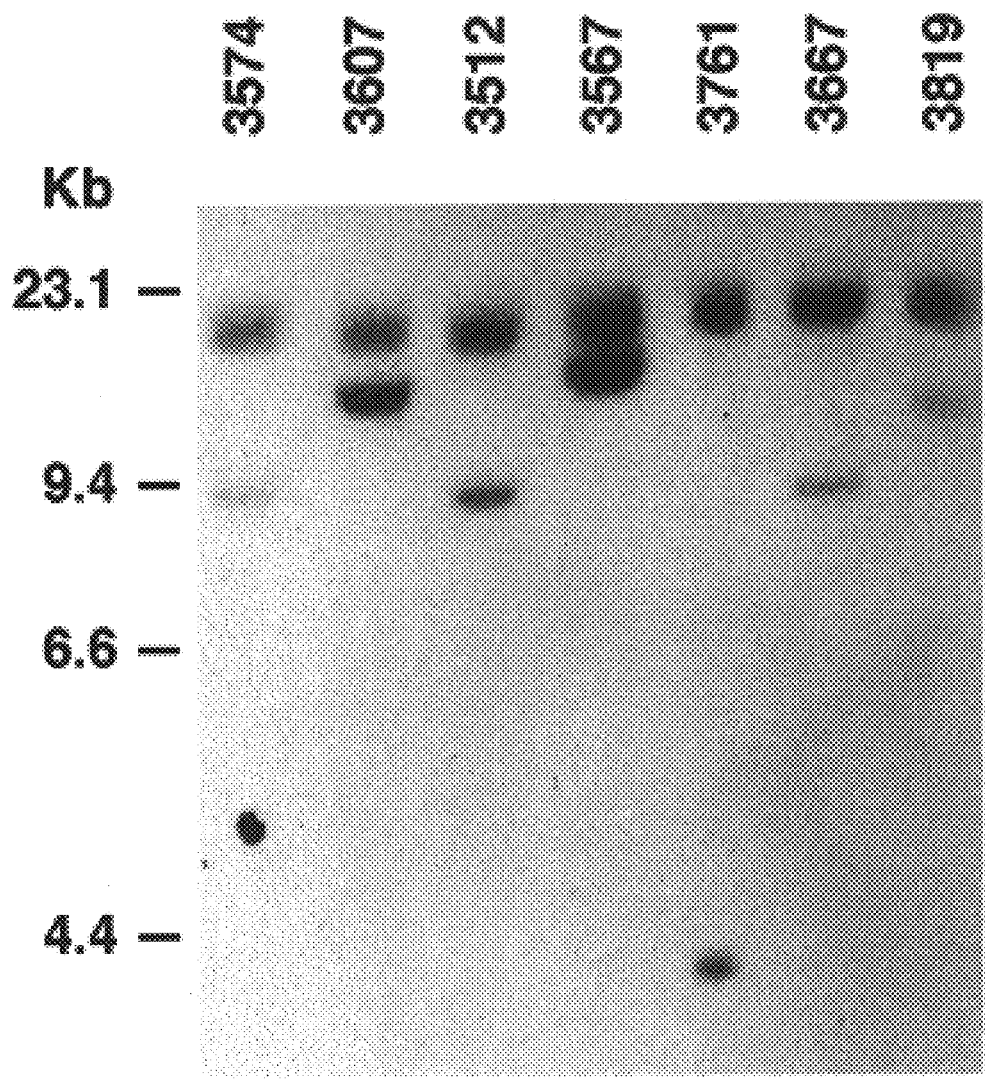
Figure 3D:
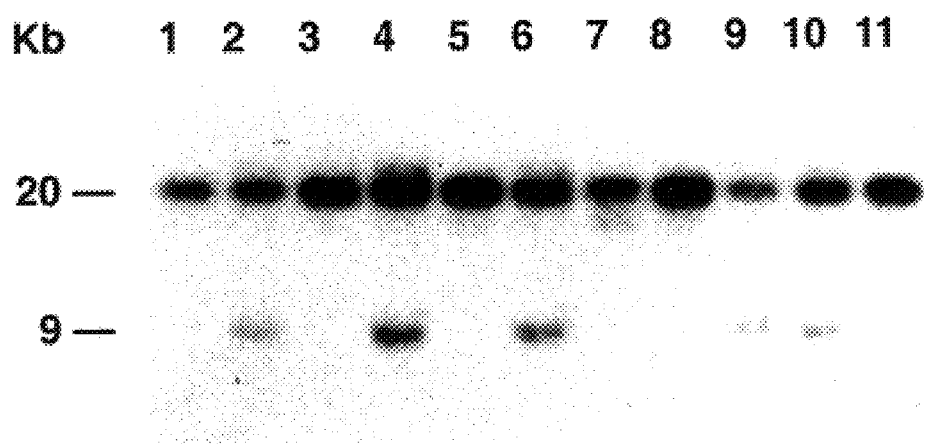
Figure 3E:
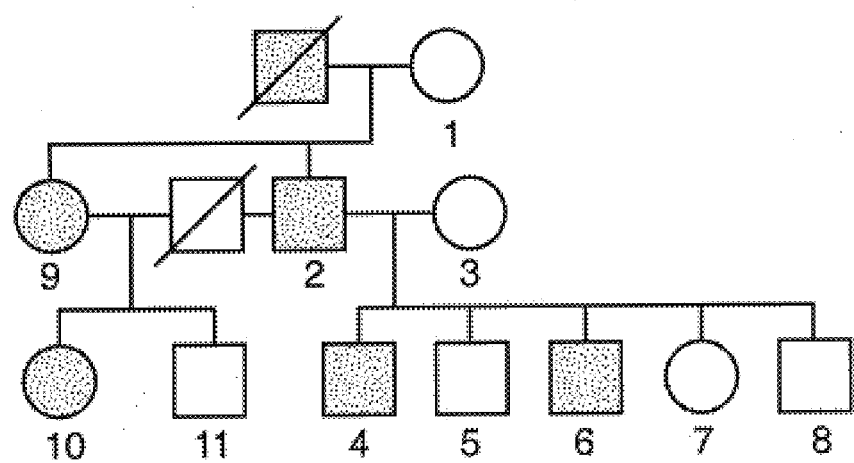

FIGS. 3A, 3B, 3C, 3D and 3E: FIGS. 3A, 3B and 3C show detection by Southern blotting analysis of rearrangement mutations in constitutional DNA of VHL affected patients using g7 cDNA as probe. FIG. 3A shows DNA from lymphoblastoid cell lines of 7 unrelated VHL patients was digested with EcoRI and analyzed by standard blotting procedures. The normal invariant band is about 20 to 22 kb, the sizes of the aberrant bands probably resulting from intragenic deletions range from 4 to 25 kb. The patients code numbers are indicated above the lanes. FIG. 3B shows DNAs from lymphoblastoid cell lines of pedigree members from a new mutation family (coded "S") digested with DraI, HindIII, and PstI. The pedigree with the position of the affected (filled circles) and predicted (hatched circle) members is shown. Males are represented by squares and females by circles. FIG. 3C shows genetic transmission of the mutant allele (the aberrant band) in a regular VHL family (coded "P") FIG. 3D. The DNAs were digested with EcoRI and analyzed by Southern blotting FIG. 3E; the pedigree is shown.

Figure 4:
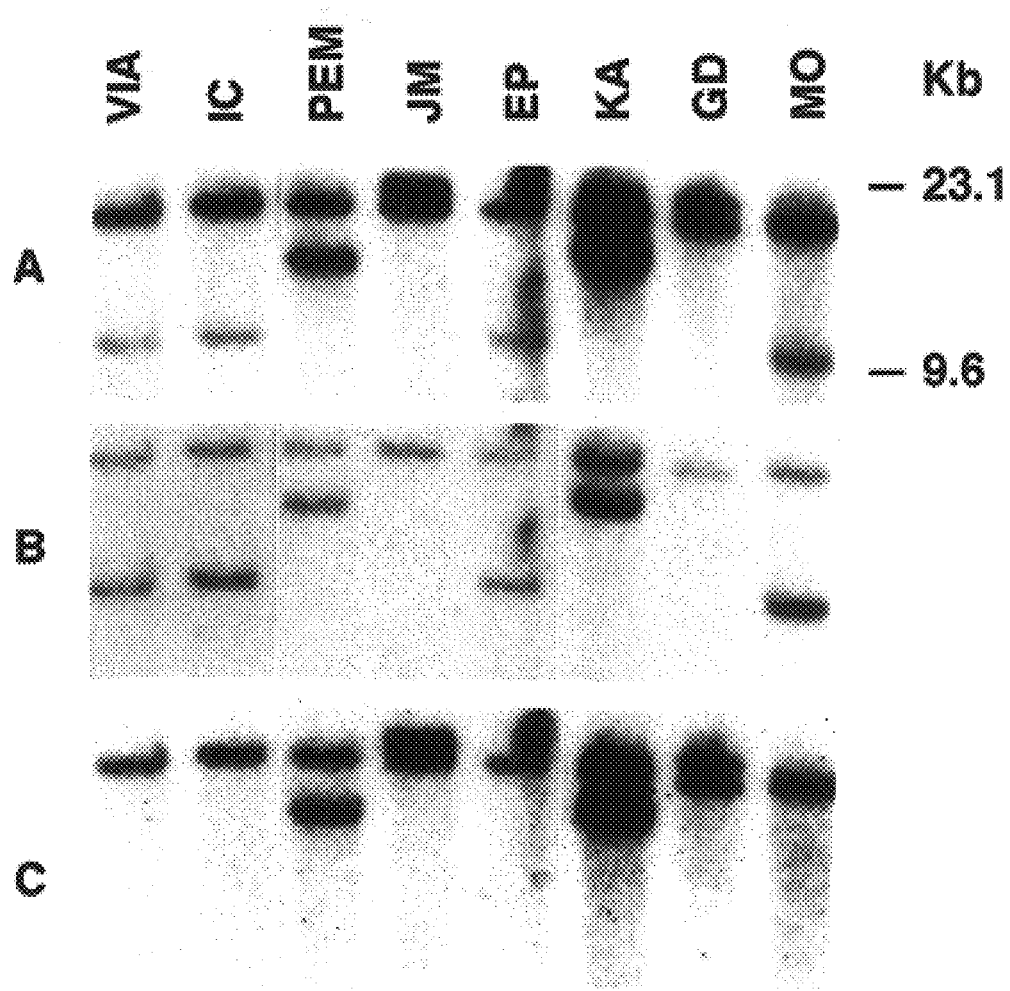

FIG. 4: FIG. 4 shows a Southern blot analysis of genomic DNA of VHL patients (only the initials of each patients name are given). The DNAs were digested with EcoRI and probed using different regions of g7 cDNA. Panel A: Total g7 cDNA probe; Panel B: 5' end probe, nucleotides 3–146; Panel C: 3' end probe nucleotides 1277–1600.

Figure 5A:
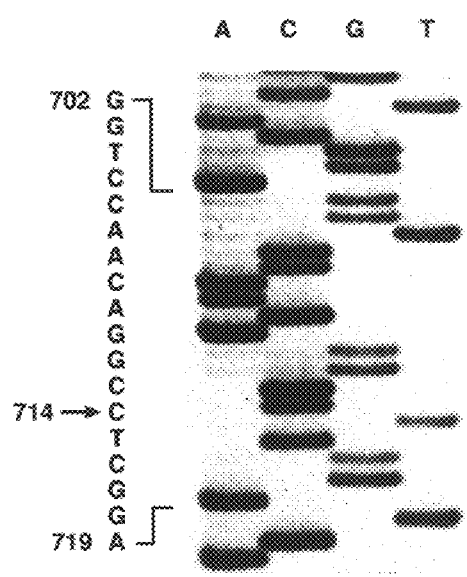
Figure 5B:
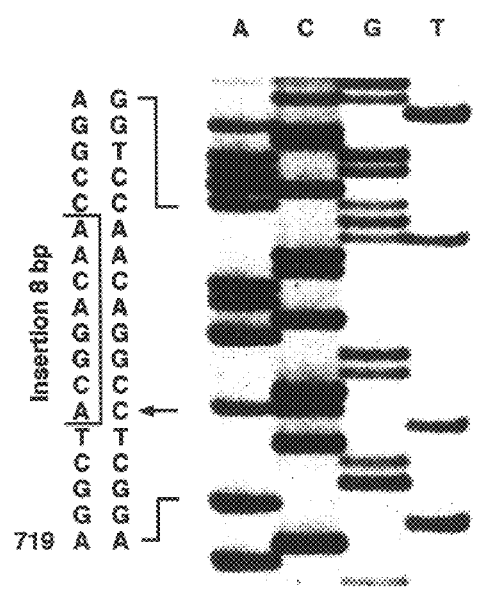

FIGS. 5A and 5B: FIGS. 5A and 5B show the results of polymerase chain reaction-single stranded conformation analysis insertion mutation (Table 1). Portions of the DNA sequencing gels are shown that display normal (FIG. 5A) and 714insTTGTCCGT mutation (FIG. 5B) sequences. The DNA sequence is of the antisense strand; therefore, the inserted bases are 5'-ACGGACAA-3'. Adjacent to the sequencing ladder are shown the positions of the insertion, and the nature of the insertion, as predicted from the sequence.

Figure 6:
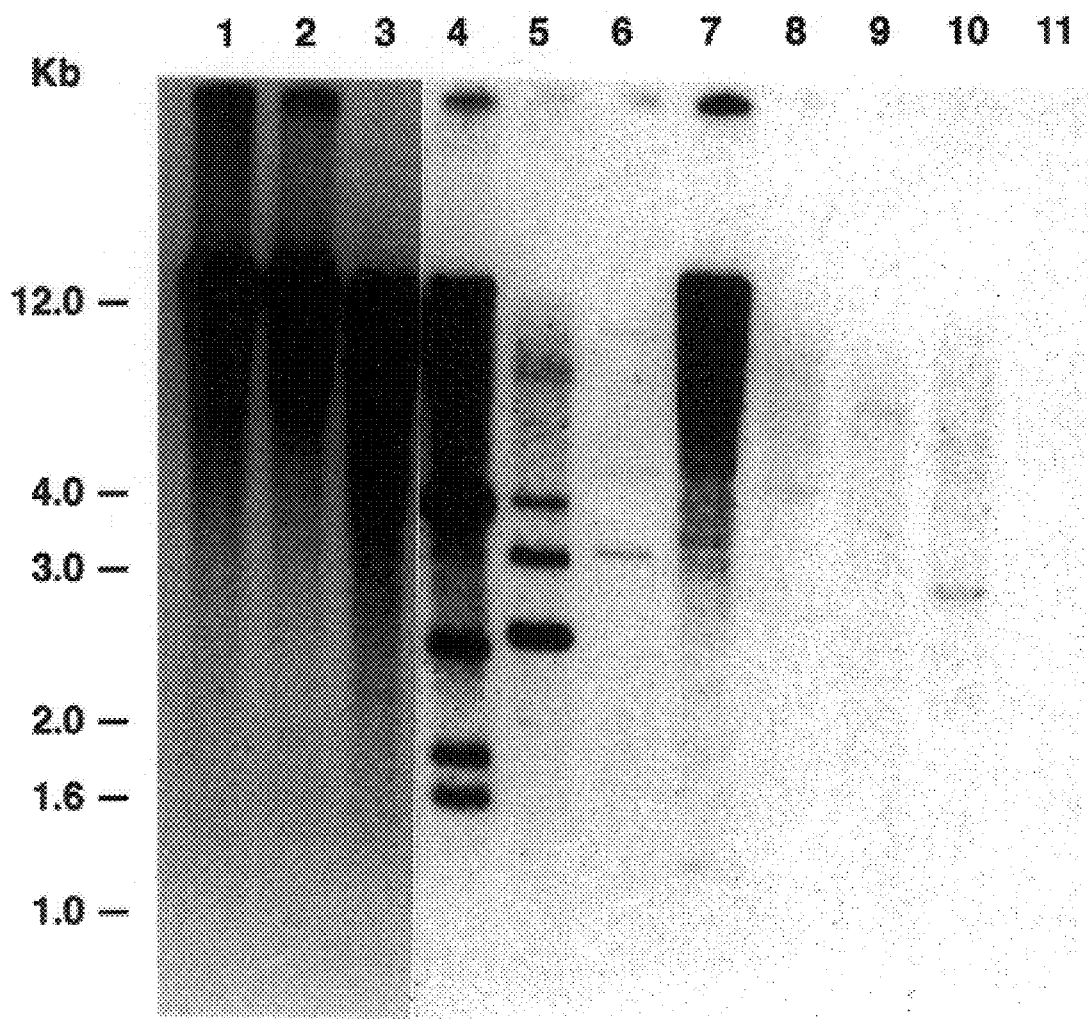

FIG. 6: FIG. 6 shows the results of a "zoo" blot illustrating evolutionary conservation of the putative VHL gene. The g7 cDNA shows cross species homology to DNA from mammals, birds, fly, and sea urchin. Lanes: 1, human (*Homo sapiens*); 2, chimpanzee (*Pan troglodytes*); 3, macaque (*Macaca fascicularis*); 4, cow (*Bovis domesticus*); 5, rat (*Rattus norvigicus*); 6, mouse (*Mus musculus*); 7, chicken (*Gallus domesticus*); 8, frog (*Xenopus laevis*); 9, fly (*Drosophila melanogaster*); 10, sea urchin (*Strongylocentrotus purpuratus*); and 11, yeast (*Saccharomyces ceriviseae*).

Figure 7A:
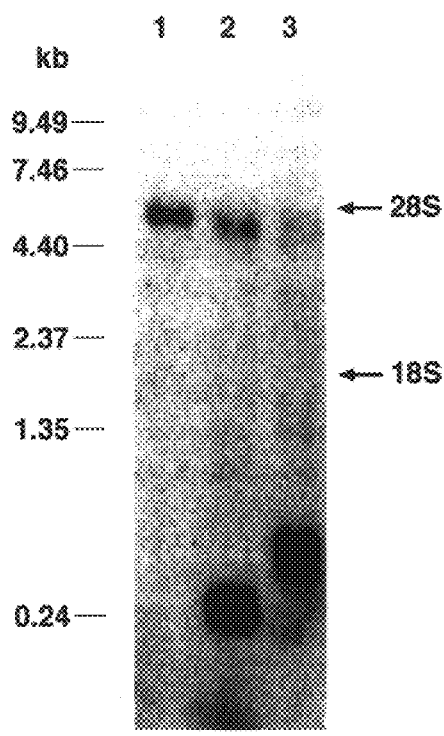
Figure 7B:
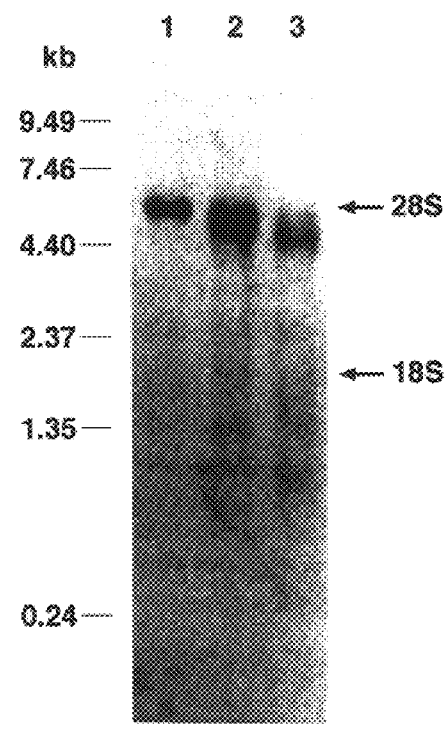
Figure 7C:
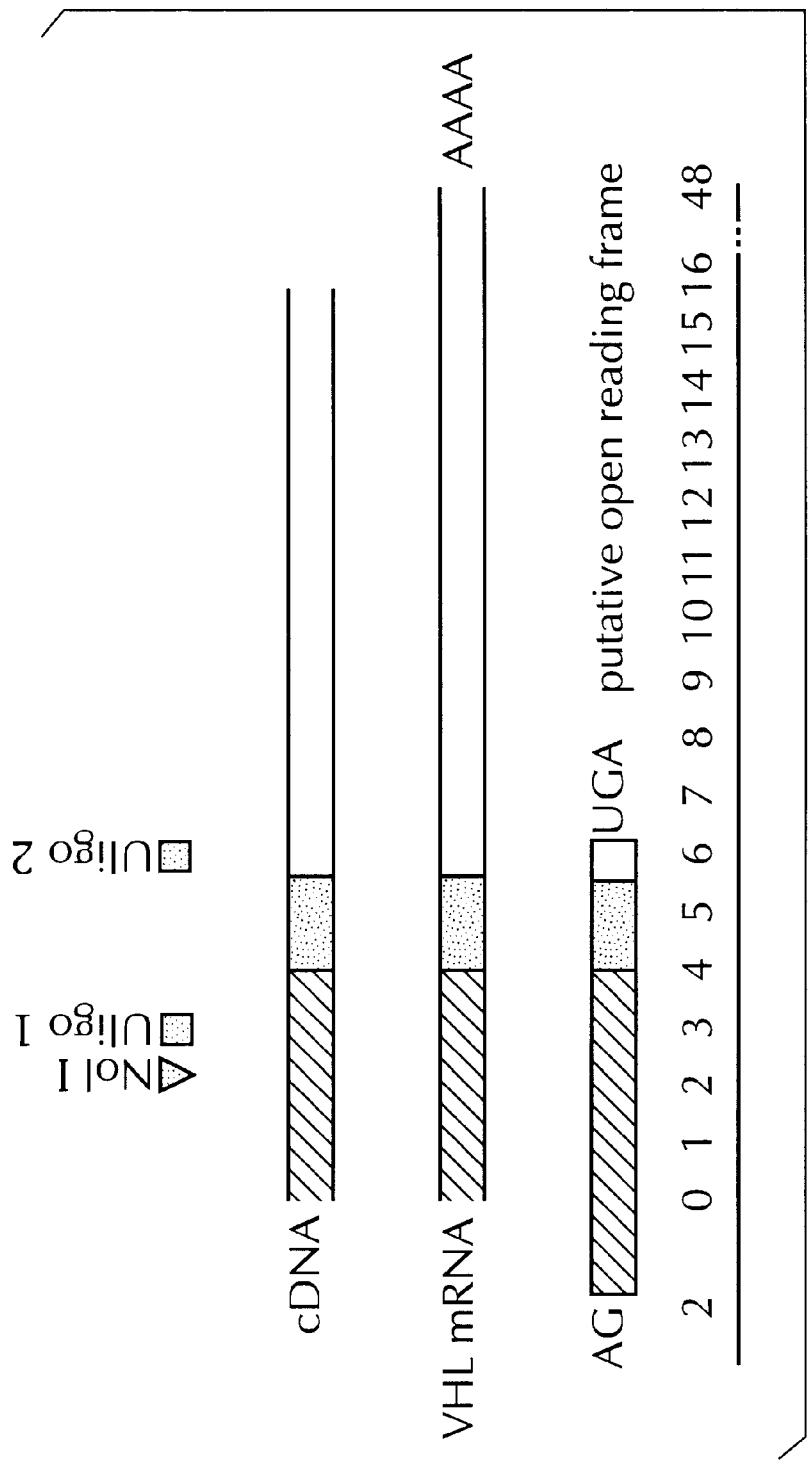

FIGS. 7A, 7B and 7C: FIGS. 7A–7C show the RNase H mapping of the VHL mRNA. FIG. 7A sets forth a Northern analysis of the RNase H digest of the VHL mRNA: 1-undigested RNA: 2-RNase H digest with oligomer 1: 3-RNase H digest with oligomer 2. Probe-extended exon 1 (bases 1–553; Latif, et al., 1993b). FIG. 7B sets forth the same plot probed with exon 3 VHL group 7 cDNA (bases 740–1810). RNA markers: 0.24–9.5 kb RNA ladder (Gibco-BRL) human 28S (5000 nt) and 18S (2000 nt) rRNAs: FIG. 7C shows the alignment of the VHL group—cDNA and VHL mRNA according to RHase H mapping; Oligomers 1 and 2 are represented by black boxes, exon 1 sequences are shown as hatched bars, exon 2 -black bars, exon 3—open bars. Putative reading frame and scale (in kb) are shown below.

Figure 8A:
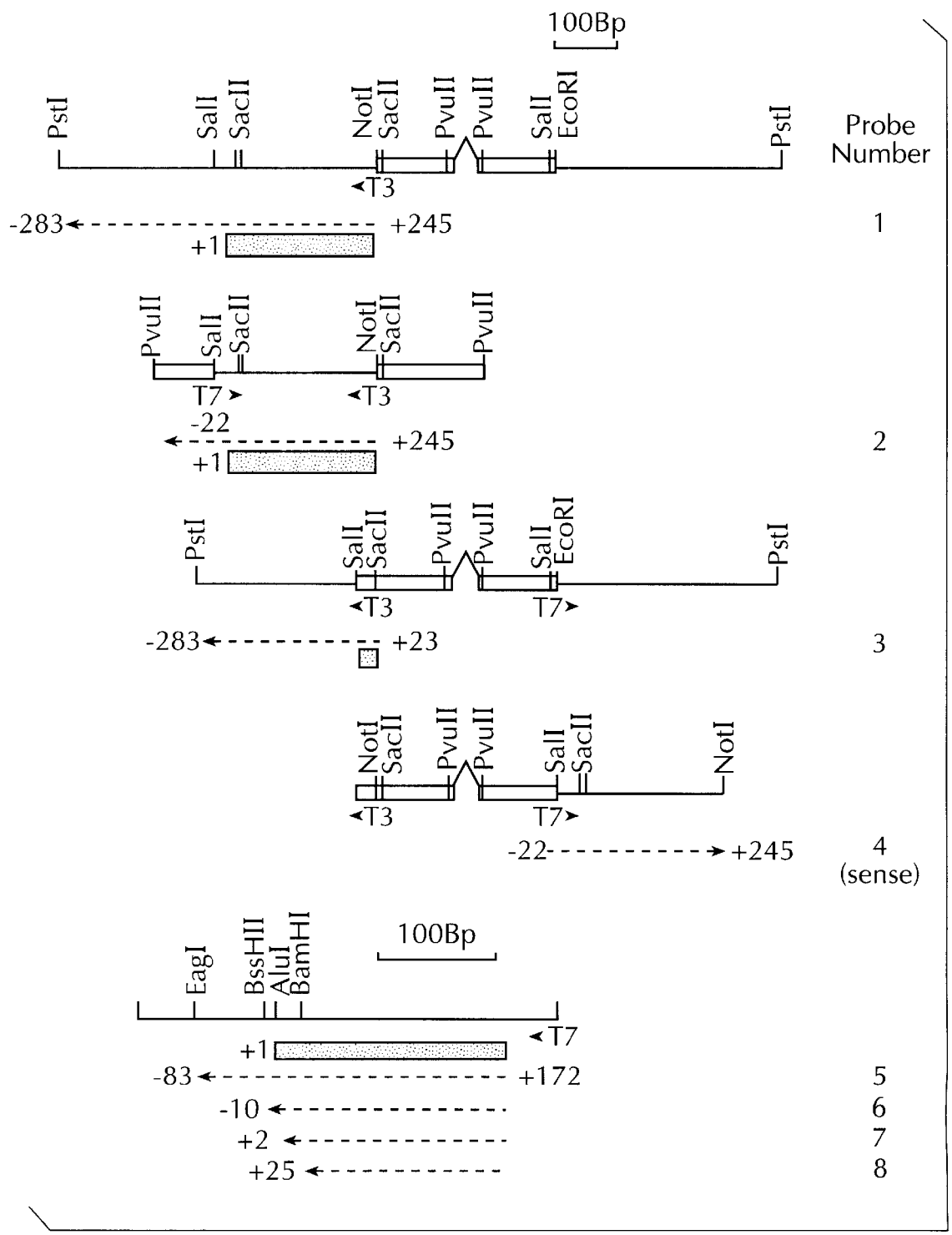
Figures 8B, 8C:
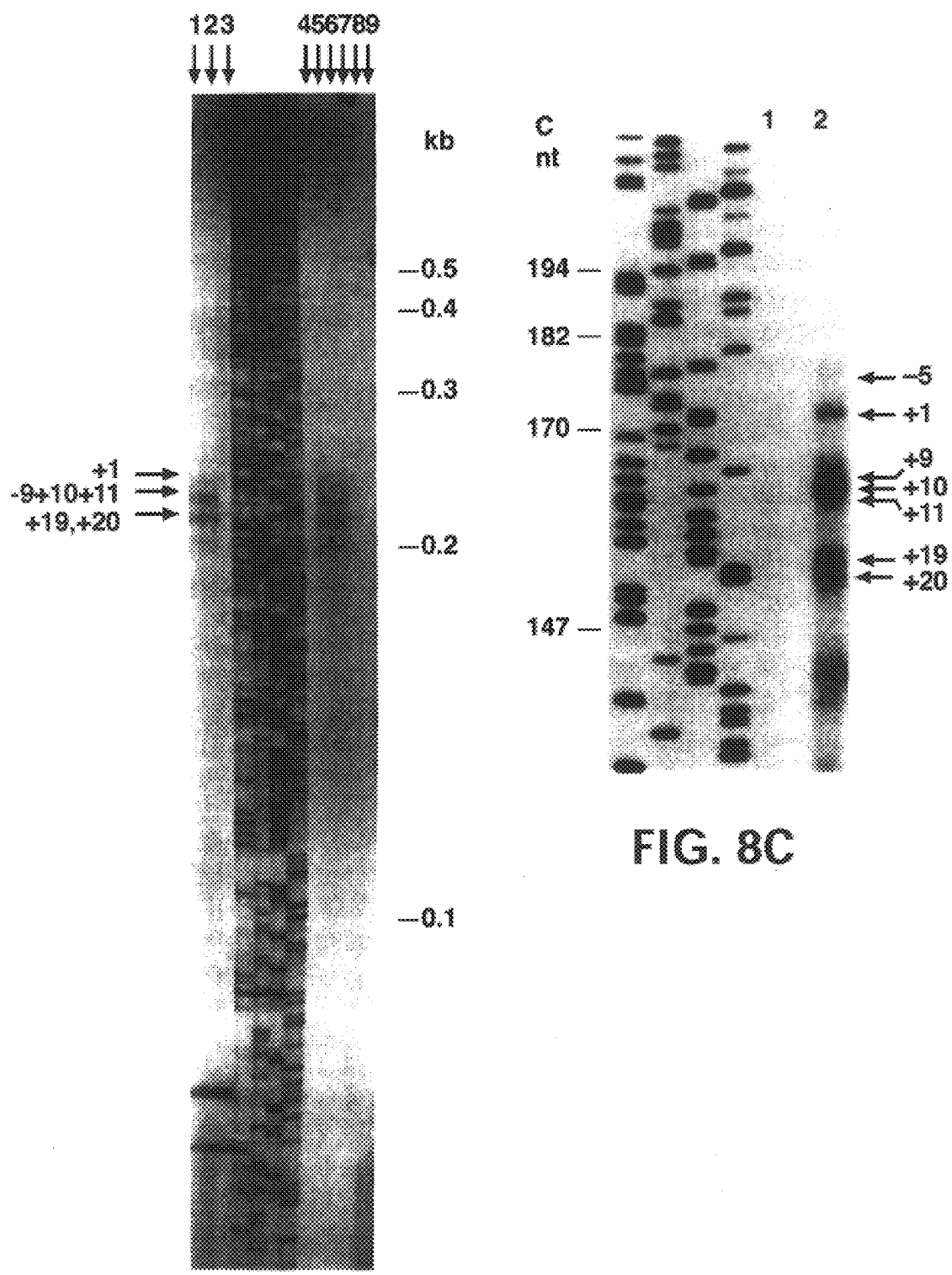

FIGS. 8A, 8B and 8C: FIGS. 8A–8C show the identification of the transcription initiation sites. FIG. 8A sets forth the templates and probes used for RNase protection assays. Genomic DNA is represented by solid line, pBluescript II SK vector is represented by an open bar, RNA probes are represented by dashed lines (with the end nucleotides numbered from VHL mRNA transcription start site +1). Probe numbers are shown in the right column. T3 and T7 promoters and their orientation are indicated. Filled bars represent protected fragments. FIG. 8B sets forth an RNase protection assay using probes 1, 2, 3 and poly(A)⁻RNA from the 293 cell line. 1, 2—probe 1 hybridized to 293 RNA (2 µg): 3—probe 1 and yeast tRNA (10 µg): 4—probe 2 and yeast tRNA; 5.6—probe 2 and 293 RNA. 7—probe 3 and yeast tRNA; 8.9—probe 3 and 293 RNA. 'Century markers' (Ambion): 500: 400: 300: 200: 100 nt C-RNase protection using probe 5 and 293 poly(A)$^{31}$ RNA 1—hybridization of the probe 5 and yeast tRNA: probe 5 and 293 RNA. Markers: protected fragments obtained after hybridization of the control sense RNA (probe 4) and probes 5: 6: 7 or 8 (194:182, 170 and 147nt, respectively).

Figure 9:
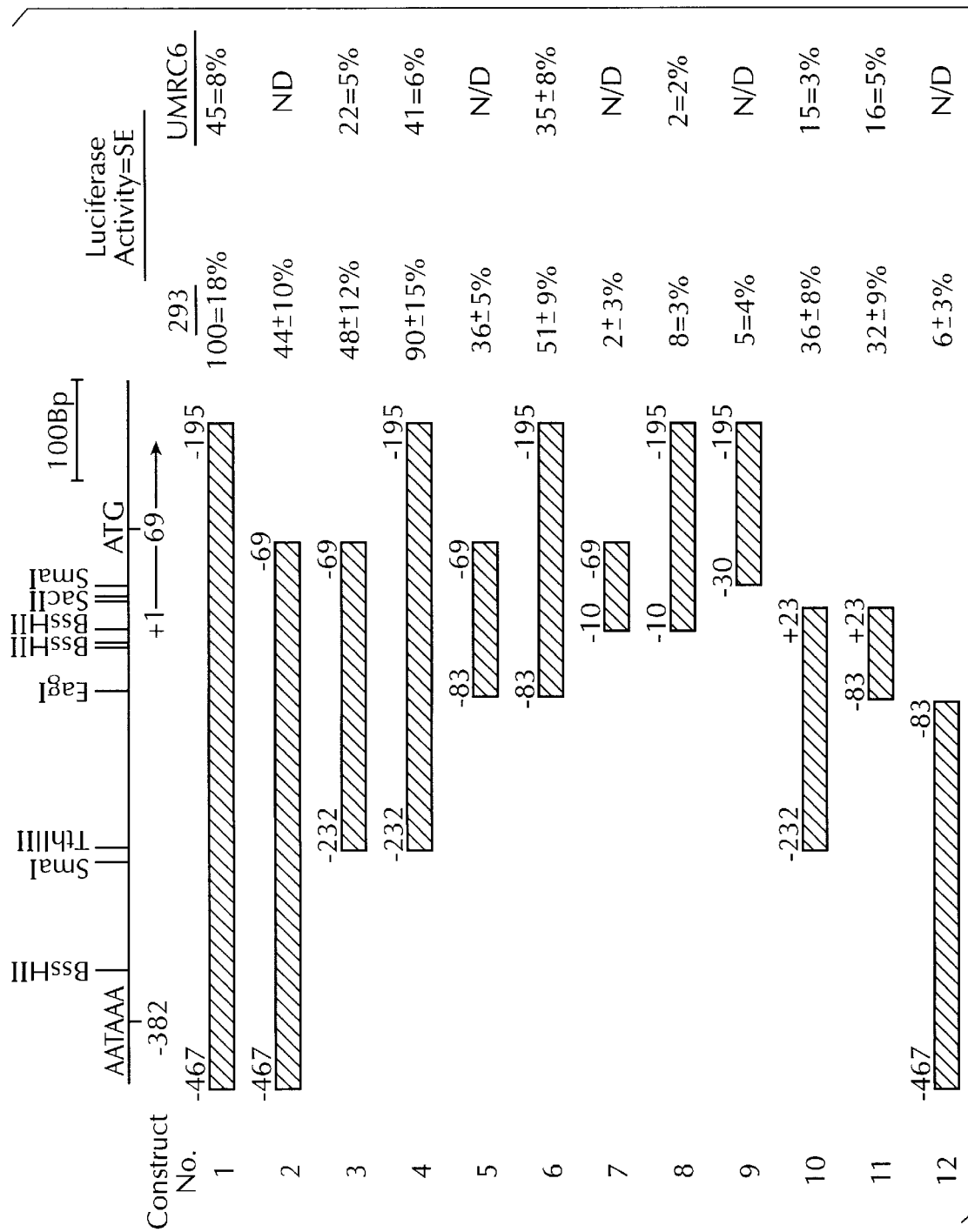

FIG. 9: FIG. 9 represents the identification of the VHL promoter region. Luciferase activity (right column) was compared to those for full length construct (residues –468/–195) which represents 100% activity in 293 cells (mean value). Restriction map of the 5' flanking genomic region is shown at the top of the Figure. The positions of transcription initiation and first methionine AUG condon are indicated.

Figure 10A:
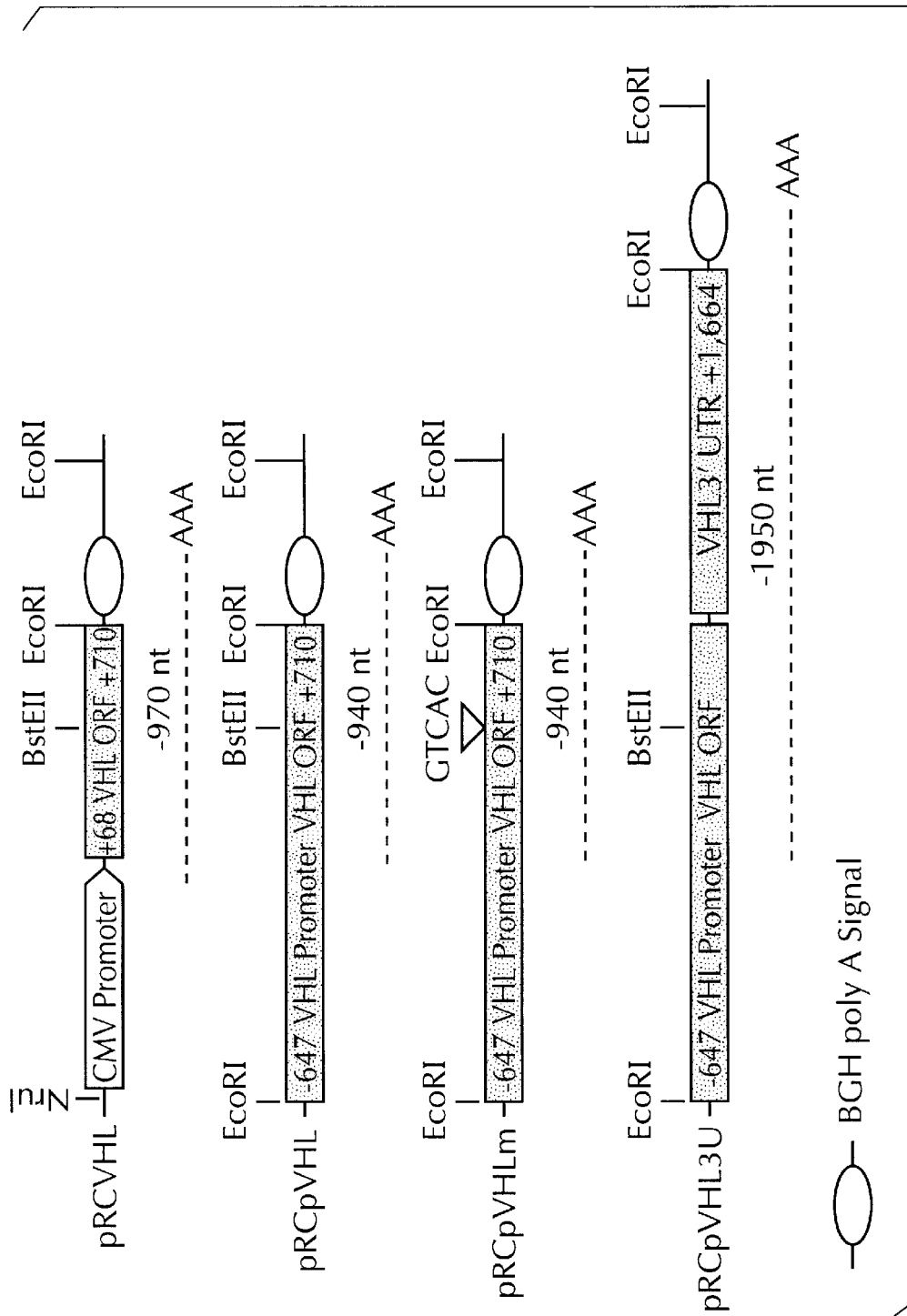
Figure 10B:
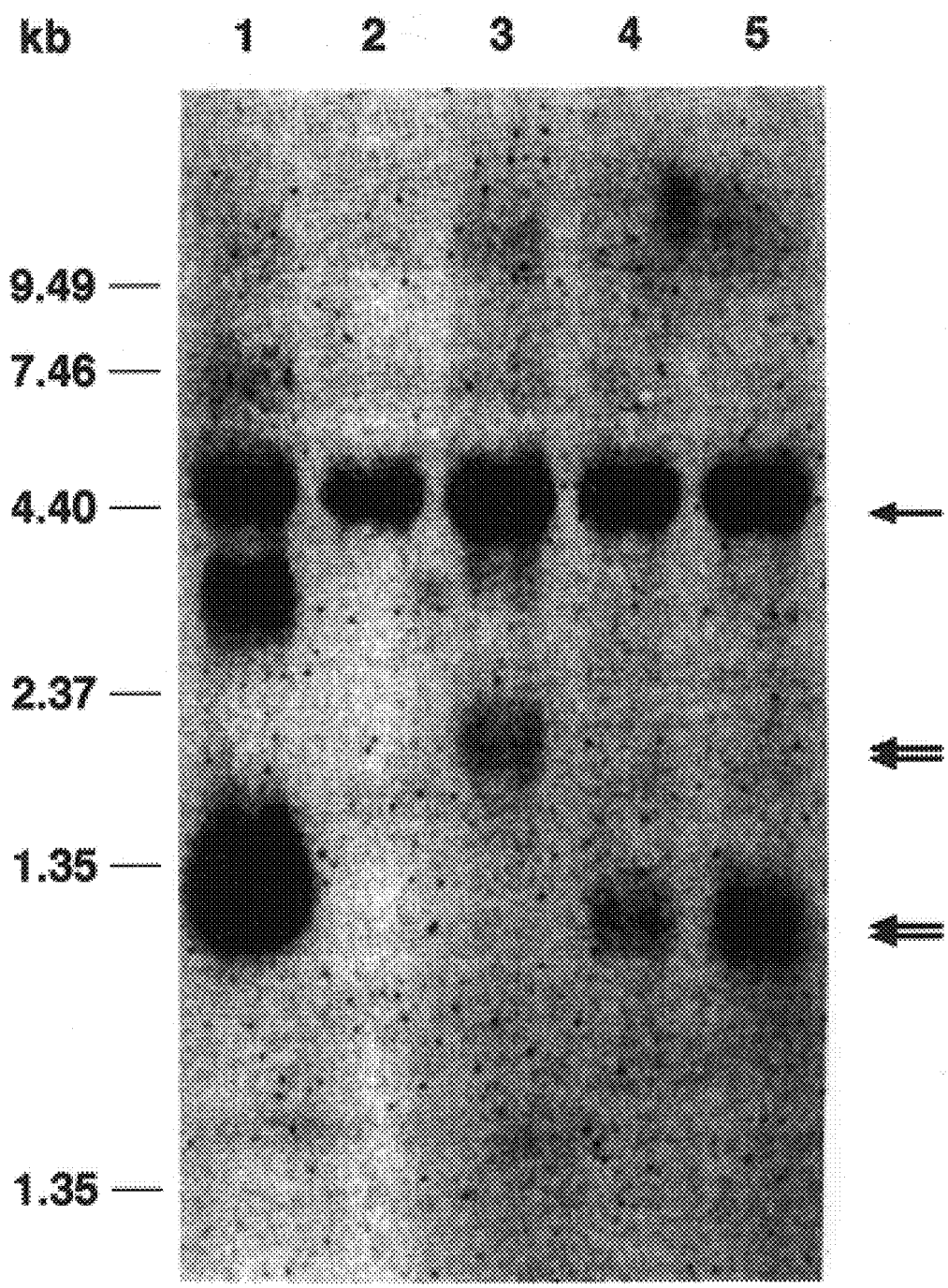

FIGS. 10A and 10B: FIGS. 10A and 10B depict VHL minigene expression in UMRC 6 cells. FIG. 10A describes expression constructs used for stable transfection of the UMRC 6 cell line. VHL sequences were shown as black bars, vector sequences—as open bars and solid lines. Predicted transcripts from VHL transgene represented by dashed line (size is indicated). FIG. 10B describes Northern analysis of the expression of the VHL transgenes. Total RNA was isolated from four pools each containing 40 to 50 colonies transfected with different expression constructs: (1) pRcHAVHL; (2) original UMRC 6 cells; (3) pRcp VHL3U; (4) pRcpVHL; (5) pRcpVHLm. Arrows indicate endogenous expression, double arrows—exogenous. Note: Previously, the size of the VHL mRNA on Northern blots was calculated as 6 to 6.5 kb (Latif, et al., 1993b) . In this study, the size of the VHL mRNA was defined more precisely as 4.4 to 5.0 kb (depending on conditions of electrophoresis). 0.24 to 9.5 kb RNA ladder (BRL) and 28S/18S human ribosomal RNA was used as a reference.

Figure 11A:
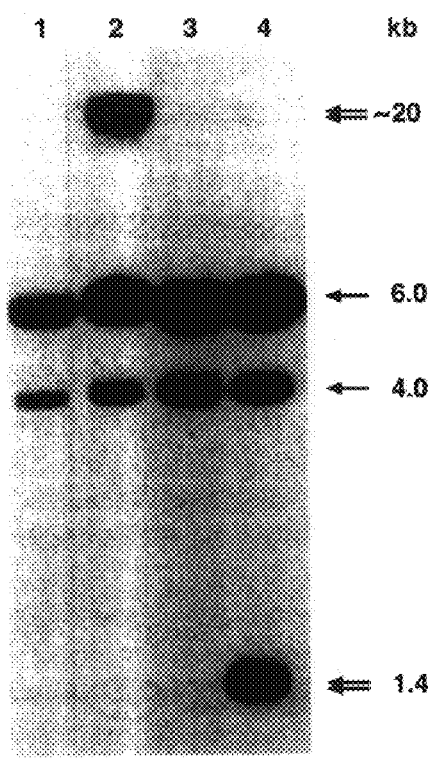
Figure 11B:
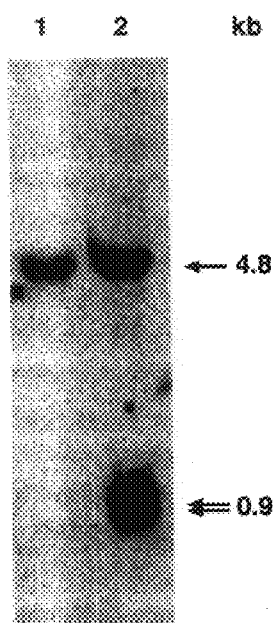

FIGS. 11A and 11B: FIGS. 11A and 11B show an analysis of the UMRC 6 clone 4 transfected with pRcpVHLm. FIG. 11A sets forth a Southern blot: 1.2—HindIII digest: 3, 4—HindIII/EcoRI digest: 1, 3—original UMRC 6 cell line: 2, 4—UMRC 6 transfected with pRcpVHLm. A single arrow indicates signals for endogenes, double arrow for exogenes. FIG. 11B sets forth a Northern blot: 1—original UMRC 6 cells: 2—UMRC 6 clone 4.

FIG. 12: FIG. 12 sets forth the sequence of the VHL promoter and surrounding genomic region. This sequence has been deposited in the GenBank database (accession no. U19763). The minimal VHL promoter is underlined. Putative SP1 and AP2 binding sites and upstream termination-polyadenylation site are shown in frame. Horizontal arrows show the start of transcription. Restriction sites for some GC-specific rare cutters are indicated. Position of the 5' end of the group 7 cDNA is shown as vertical arrow. The putative upstream splice acceptor site is double underlined. The first AUG codon in VHL mRNA is shown in a black box.

FIG. 13: FIG. 13 sets forth the nucleic acid sequences of the partial intron sequences of the VHL disease gene. The upper case letters depict the exon sequences and the lower case letters depict the intron sequences.

DETAILED DESCRIPTION OF THE INVENTION

The present invention relates to the VHL disease gene, its corresponding cDNA and primers corresponding to the VHL wild-type gene sequence. Recently, the region of human chromosome 3 containing the VHL disease gene has been cloned by genomic walking with yeast artificial chromosomes (YACS) and the cloned DNA recovered with cosmids from a chromosome 3 specific library. The phage 191 which contains the VHL disease gene was deposited with the American Type Culture Collection (ATCC), 12301 Parklawn Drive, Rockville, Md. 20852 on May 13, 1993 and has been granted ATCC deposit number 69311. This VHL gene represents the wild-type VHL gene where wild-type means the gene not causing VHL disease or other disease associated with the VHL gene.

The present invention is also directed to a cDNA corresponding to the VHL gene. This cDNA sequence, designated g7, is set forth below as SEQ ID NO: 1 and was deposited with the American Type Culture Collection on May 13, 1993, and has been granted ATCC deposit number 69312. This cDNA also has GenBank accession No. L15409.

```
CCTCGCCTCC GTTACAACAG CCTACGGTGC TGGAGGATCC TTCTGCGCAC      50

GCGCACAGCC TCCGGCCGGC TATTTCCGCG AGCGCGTTCC ATCCTCTACC     100

GAGCGCGCGC GAAGACTACG GAGGTCGACT CGGGAGCGCG CACGCAGCTC     150

CGCCCCGCGT CCGACCCGCG GATCCCGCGG CGTCCGGCCC GGGTGGTCTG     200

GATCGCGGAG GGAATGCCCC GGAGGGCGGA GAACTGGGAC GAGGCCGAGG     250

TAGGCGCGGA GGAGGCAGGC GTCGAAGAGT ACGGCCCTGA AGAAGACGGC     300

GGGGAGGAGT CGGGCGCCGA GGAGTCCGGC CCGGAAGAGT CCGGCCCGGA     350

GGAACTGGGC GCCGAGGAGG AGATGGAGGC CGGGCGGCCG CGGCCCGTGC     400

TGCGCTCGGT GAACTCGCGC GAGCCCTCCC AGGTCATCTT CTGCAATCGC     450

AGTCCGCGCG TCGTGCTGCC CGTATGGCTC AACTTCGACG GCGAGCCGCA     500

GCCCTACCCA ACGCTGCCGC CTGGCACGGG CCGCCGCATC CACAGCTACC     550

GAGGTCACCT TTGGCTCTTC AGAGATGCAG GGACACACGA TGGGCTTCTG     600

GTTAACCAAA CTGAATTATT TGTGCCATCT CTCAATGTTG ACGGACAGCC     650

TATTTTTGCC AATATCACAC TGCCAGTGTA TACTCTGAAA GAGCGATGCC     700

TCCAGGTTGT CCGGAGCCTA GTCAAGCCTG AGAATTACAG GAGACTGGAC     750

ATCGTCAGGT CGCTCTACGA AGATCTGGAA GACCACCCAA ATGTGCAGAA     800

AGACCTGGAG CGGCTGACAC AGGAGCGCAT TGCACATCAA CGGATGGGAG     850

ATTGAAGATT TCTGTTGAAA CTTACACTGT TTCATCTCAG CTTTTGATGG     900

TACTGATGAG TCTTGATCTA GATACAGGAC TGGTTCCTTC CTTAGTTTCA     950

AAGTGTCTCA TTCTCAGAGT AAAATAGGCA CCATTGCTTA AAAGAAAGTT    1000

AACTGACTTC ACTAGGCATT GTGATGTTTA GGGGCAAACA TCACAAAATG    1050

TAATTTAATG CCTGCCCATT AGAGAAGTAT TTATCAGGAG AAGGTGGTGG    1100

CATTTTTGCT TCCTAGTAAG TCAGGACAGC TTGTATGTAA GGAGGTTTAT    1150

ATAAGTAATT CAGTGGGAAT TGCAGCATAT CGTTTAATTT TAAGAAGGCA    1200

TTGGCATCTG CTTTTAATGG ATGTATAATA CATCCATTCT ACATCCGTAG    1250

CGGTTGGTGA CTTGTCTGCC TCCTGCTTTG GAAGACTGA GGCATCCGTG     1300

AGGCAGGGAC AAGTCTTTCT CCTCTTTGAG ACCCCAGTGC CTGCACATCA    1350
```

```
                          -continued
TGAGCCTTCA GTCAGGGTTT CTCAGAGGAA CAAACCAGGG GACACTTTGT    1400

TAGAAAGTGC TTAGAGGTTC TGCCTCTATT TTTGTTGGGG GGTGGGAGAG    1450

GGGACCTTAA AATGTGTACA GTGAACAAAT GTCTTAAAGG GAATCATTTT    1500

TGTAGGAAGC ATTTTTTATA ATTTTCTAAG TCGTGCACTT TCTCGGTCCA    1550

CTCTTGTTGA AGTGCTGTTT TATTACTGTT TCTAAACTAG GATTGACATT    1600

CTACAGTTGT GATAATAGCA TTTTTGTAAC TTGCCATCCG CACAGAAAAT    1650

ACGAGAAAAT CTGCATGTTT GATTATAGTA TTAATGGACA AATAAGTTTT    1700

TGCTAAATGT GAGTATTTCT GTTCCTTTTT GTAAATATGT GACATTCCTG    1750

ATTGATTTGG GTTTTTTTGT TGTTGTTGTT TTGTTTTGTT TTGTTTTTTT    1800

GGGATGGAGG GAATTC                                        1816
```

The abbreviations used for the nucleotides are those standardly used in the art.

The deduced amino acid sequence of the g7 cDNA is shown as SEQ ID NO: 2 below and starts at nucleotide 1 of SEQ ID NO:1 and extends 851 nucleotides.

```
Pro Arg Leu Arg Tyr Asn Ser Leu Arg Cys Trp Arg Ile Leu Leu
                 5                  10                  15

Arg Thr Arg Thr Ala Ser Gly Arg Leu Phe Pro Arg Ala Arg Ser
                20                  25                  30

Ile Leu Tyr Arg Ala Arg Ala Lys Thr Thr Glu Val Asp Ser Gly
                35                  40                  45

Ala Arg Thr Gln Leu Arg Pro Ala Ser Asp Pro Arg Ile Pro Arg
                50                  55                  60

Arg Pro Ala Arg Val Val Trp Ile Ala Glu Gly Met Pro Arg Arg
                65                  70                  75

Ala Glu Asn Trp Asp Glu Ala Glu Val Gly Ala Glu Glu Ala Gly
                80                  85                  90

Val Glu Glu Tyr Gly Pro Glu Glu Asp Gly Gly Glu Glu Ser Gly
                95                  100                 105

Ala Glu Glu Ser Gly Pro Glu Glu Ser Gly Pro Glu Glu Leu Gly
                110                 115                 120

Ala Glu Glu Glu Met Glu Ala Gly Arg Pro Arg Pro Val Leu Arg
                125                 130                 135

Ser Val Asn Ser Arg Glu Pro Ser Gln Val Ile Phe Cys Asn Arg
                140                 145                 150

Ser Pro Arg Val Val Leu Pro Val Trp Leu Asn Phe Asp Gly Glu
                155                 160                 165

Pro Gln Pro Tyr Pro Thr Leu Pro Pro Gly Thr Gly Arg Arg Ile
                170                 175                 180

His Ser Tyr Arg Gly His Leu Trp Leu Phe Arg Asp Ala Gly Thr
                185                 190                 195

His Asp Gly Leu Leu Val Asn Gln Thr Glu Leu Phe Val Pro Ser
                200                 205                 210

Leu Asn Val Asp Gly Gln Pro Ile Phe Ala Asn Ile Thr Leu Pro
                215                 220                 225

Val Tyr Thr Leu Lys Glu Arg Cys Leu Gln Val Val Arg Ser Leu
                230                 235                 240

Val Lys Pro Glu Asn Tyr Arg Arg Leu Asp Ile Val Arg Ser Leu
                245                 250                 255
```

```
Tyr Glu Asp Leu Glu Asp His Pro Asn Val Gln Lys Asp Leu Glu
                260                 265                 270

Arg Leu Thr Gln Glu Arg Ile Ala His Gln Arg Met Gly Asp
                275                 280
```

The present invention is also directed to intron sequences of the wild-type VHL disease gene. These intron sequences are set forth below as SEQ. ID. NO: 3, SEQ. ID. NO: 4, and SEQ. ID. NO: 5. The lower case letters represent the intron sequences, and the upper case letters represent the surrounding exon sequences.

```
5'-TACCCAACG CTGCCGCCTG GCACGGGCCG CCGCATCCAC AGCTACCGAG      SEQ. ID. NO: 3 gtacgggccc ggcgcttagg cccgacccag caggacgata gcacggtcta agcccctcta ccgccccggg gtccattcag acggggaact aggcccttg aggcaggaca catccagggt-3'

5'-ctcctgacct ctatgatccg cctgcctcgg cctccaaagt gctgggatta    SEQ. ID. NO: 4 caggtgtggg ccaccgtgcc cagccaccgg tGTGGCTCtt taacaacctt tgcttgtccc gatagGTCAC CTTTGGCTCT TCAGAGATGC AGGGACACAC

GATGGGCTTC TGGTTAACCA AACTGAATTA TTTGTGCCAT CTCTCAATGT

TGACGGACAG CCTATTTTTG CCAATATCAC ACTGCCAGt actgacgttt tacttttaa aaagataagg ttgttgtggt aagtacagga tagaccactt gaaaaattaa gcccagttct caatttttgc ctgatgtcag gcacggtatc caatcttttt gtatcctatt ctctaccata aataaaatgg aagtgatgat ttt-3'

5'-ctacagaagg catgaacacc atgaagtgtc catagggcc acagcataca     SEQ. ID. NO: 5 cactgccaca tacatgcact cacttttttt ctttaaccta aaagtgaaga tccatcagta gtacaggtag ttgttggcaa aagcctcttg ttcgttcctt gtactgagac cctagtctgc cactgaggat ttggtttttg ccc-3'
```

EXAMPLE 2

Isolation of a cDNA Corresponding to VHL Disease Gene

Screening cDNA Libraries. A λgt11 teratocarcinoma library (gift of Dr. Maxine Singer, National Cancer Institute) was screened by plaque hybridization (Sambrook, J. et al. (1989)) to $10^6$ filter-immobilized cDNA phage clones at a density of $4 \times 10^4$ pfu/150-mm filter. FIG. 1B shows the position of the g7 cDNA isolated by screening the λgt11 teratocarcinoma cDNA library with a conserved Fkb fragment at the centromeric end of cos11 used as a probe in the screening. The orientation of the g7 cDNA was established by sequencing and restriction mapping to the contig. The beginning of the smallest constitutional deletion is indicated by an asterisk and line. Restriction sites: B, Bam HI; E, Eco RI; N, Not I; Nr, Nru I; M, Mlu I.

cDNA Sequence and Sequence Analysis. The g7 cDNA clone was sub-cloned into the Bluescript KS (+) plasmid (Stratagene, La Jolla, Calif.). Double-stranded plasmid DNA was used in sequencing reactions performed with Taq Dye Deoxy terminator cycle sequencing kits (Applied Biosystems, Inc.). All sequences were obtained by running the reactions in an ABI 373A automatic sequencing system (Applied Biosystems, Inc.). Initial sequencing was performed with T3 and T7 primers, and "walking" primers were then constructed to continue sequencing. The cDNA clone was sequenced multiple times in one orientation or both orientations. Database searching, sequence editing, sequence assembly, and sequence analysis were carried out with the University of Wisconsin Genetics Computer Group sequence analysis software package, version 7.0 (Devereaux, J. et al. Nucl. Acids Rev. (1984) 12:387–395). The sequence of the g7 cDNA is shown in SEQ ID No. 1. This cDNA was deposited with the ATCC on May 13, 1993. The cDNA sequence revealed an open reading frame (ORF) of 284 amino acids indicating that the rest represents part of the 3' untranslated region of the mRNA. This ORF showed a high probability score (>95%) for being a protein coding sequence Fickett, J. W., Nucl. Acids Rev. (1982) 10:5303). Neither the nucleotide nor the predicted amino acid sequences showed any significant homology to genes or proteins in the databases.

EXAMPLE 3

Detection of g7-Specific mRNA Expression in Target Tissues

RNA Preparation and Northern Blotting Analysis. To identify the VHL gene, the g7 loci was evaluated by analyzing its expression in target tissues.

The expression pattern of the g7 gene was examined by Northern (RNA) blotting. FIG. 2A shows a low resolution blot where each lane contains poly A$^+$ mRNA (2 µg) from: lane 1, fetal brain; lane 2, adult brain; lane 3, fetal kidney;

lane 4, adult kidney; lane 5, adult cerebellum; lane 6, adult adrenal; and lane 7, adult prostate while FIG. 2B shows a high resolution blot of 1 μg of poly A+ mRNA from tissues as indicated in FIG. 2A. The sizes of the transcripts were determined from the position of the 28S and 18S rRNA bands of total RNA run on the same gel. Transcripts were observed in all human tissues tested, including brain and kidney, tissues frequently affected in VHL disease. The transcripts were of two distinct sizes, 6 and 6.5 kb, and were expressed in a tissue-specific and developmentally selective manner, i.e. only 6 kb or the 6.5 kb species was expressed in fetal brain and fetal kidney, while both were expressed in adult tissues. The two transcripts may represent alternatively spliced forms of g7 mRNA.

EXAMPLE 4

Detection of Mutations of the VHL Disease Gene Associated with VHL Disease and Related Diseases RT-PCR Studies of Gene Expression. In order to detect mutations in constitutional DNA of affected patients in pedigrees and in new mutation patients, an extensive search for mutations (i.e. small intragenic and nonoverlapping deletions or insertions) which were of the loss-of-function type was conducted in constitutional DNA derived from 221 unrelated VHL patients. Southern blot analysis of genomic DNA isolated from the blood (Sambrook, J. et al. (1989)) of seven patients and then digested with EcoRI is shown in FIG. 3A. This blot was probed using the g7 cDNA as probe. This probe has been shown to detect a single invariant 20–22 kb EcoRI fragment in normal DNA, as determined by previous tests on more than 100 unrelated DNA samples provided by Centre d'Etude du Polymorphisme Humain (CEPH). A high incidence (≧12%) of aberrant bands was observed with the bands ranging in size from 4 to 25 kb (FIG. 3A), and these VHL patients were thus classified as new mutations.

In order to determine that the single aberrant bands originating from the 20–22 kb invariant fragment were deletions or insertions within this fragment or deletions removing the flanking EcoRI sites, Southern blot analysis was conducted with several other restriction enzyme digests besides EcoRI (BamHI, BglI, BglII, DraI, EcoRV, HindIII, PstI, and PvuII). The results of the Southern analysis with a few of these enzymes is shown in FIG. 3B. These results demonstrated that the mutations were transmitted with the disease. FIGS. 3C–3C show the results of Southern blotting analysis of DNA isolated form a regular VHL family (coded "P") and digested with EcoRI. The results clearly demonstrate transmission of the mutant allele (the aberrant band) in this VHL family.

EXAMPLE 5

Detection and Mapping of Deletions of the VHL Disease Gene

To prove the presence of deletions and to map them precisely, subfragments representing regions of the g7 cDNA generated by PCR were used as probes in Southern blotting analysis of genomic DNA isolated from blood of VHL patients and digested with EcoRI. (FIG. 4, where the probes used in each panel are: Panel A, total g7 cDNA; Panel B, nucleotides 3–146 of g7 cDNA; and Panel C, nucleotides 1277–1600 of g7 cDNA). The results unequivocally demonstrated that 18 of the rearrangements were deletions as only part of the cDNA failed to detect the novel band in each patient (FIG. 4).

These deletions could then be classified into three groups, as shown in Table 1.

TABLE 1

Deletion analysis of VHL patients with aberrant bands at the VHL locus (detected by g7 cDNA).

| Patient Code | Probe: cDNA 5'->3' residue(s) | | | | | | Aberrant band (kb) | Apparent Deletion Size (kb) |
|---|---|---|---|---|---|---|---|---|
| | 3–146 | 169–391 | 291–501 | 585–940 | 921–1231 | 1277–1600 | | |
| 3567 | ND | ND | ND | ND | ND | ND | 14 | ? |
| 3607 | ND | ND | ND | ND | ND | ND | 12 | ? |
| 3639 | ND | ND | ND | ND | ND | ND | 14 | ? |
| 3648 | ND | ND | ND | ND | ND | ND | 13 | ? |
| 3654 | ND | ND | ND | ND | ND | ND | 14 | ? |
| JD | ND | ND | ND | ND | ND | ND | 17 | ? |
| PEM | ND | ND | ND | ND | ND | ND | 15 | ? |
| MS | ND | ND | ND | ND | ND | ND | 15 | ? |
| KA | ND | ND | ND | ND | ND | ND | 15 | ? |
| 3547 | D | D | D | ND | ND | ND | 23–25 | 15–18 |
| JM | D | D | D | ND | ND | ND | 23–25 | 15–18 |
| GD | D | D | D | ND | ND | ND | 23–25 | 15–18 |
| 3512 | ND | ND | ND | ND | D | D | 10 | 11 |
| 3516 | ND | ND | ND | ND | D | D | 10 | 11 |
| 3557 | ND | ND | ND | ND | D | D | 10 | 11 |
| 3574 | ND | ND | ND | ND | D | D | 10 | 11 |
| VIA | ND | ND | ND | ND | D | D | 10 | 11 |
| IC | ND | ND | ND | ND | D | D | 10 | 11 |
| NE | ND | ND | ND | ND | D | D | 10 | 11 |
| EP | ND | ND | ND | ND | D | D | 10 | 11 |
| MO | ND | ND | ND | ND | D | D | 10 | 11 |
| 3569 | ND | ND | ND | D | D | D | 12 | 9 |
| 3667 | ND | ND | ND | D | D | D | 10 | 11 |
| 3761 | ND | ND | ND | D | D | D | 4 | 17 |
| 3819 | ND | ND | ND | D | D | D | 12 | 9 |

TABLE 1-continued

Deletion analysis of VHL patients with aberrant bands at the
VHL locus (detected by g7 cDNA).

| Patient Code | Probe: cDNA 5'->3' residue(s) | | | | | Aberrant band (kb) | Apparent Deletion Size (kb) |
|---|---|---|---|---|---|---|---|
| | 3–146 | 169–391 | 291–501 | 585–940 | 921–1231 | 1277–1600 | | |

ND = Not deleted
D = Deleted

The finding of three overlapping deletions within the same cDNA provides strong evidence for the identification of the g7 cDNA as the VHL gene.

EXAMPLE 6

Detection of Intragenic Deletions or Insertions by PCR-SSCP and RT-PCR

To find intragenic deletions or insertions, genomic DNA isolated from VHL patient lymphoblastoid cell lines (Lymphoblastoid cells were immortalized by transformation with Epstein Barr Virus according to standard protocols (Nilison, K. et al., Adv. Cancer Res. (1982) 37:319–380)) was analyzed for alterations by PCR-single-strand-conformational polymorphism (PCR-SSCP) analysis using primers shown in SEQ. ID. NO. 7 thru SEQ. ID. NO. 12 and RNA isolated from sporadic renal cell carcinoma (RCC) cell lines (Anglard, P. et al. Cancer Res. (1992) 52:348–356) was analyzed by reverse transcription-polymerase chain reaction (RT-PCR). The primers used for RT-PCR of the RCC cell lines are shown as SEQ. ID. NO. 50 thru SEQ. ID. NO. 53:

```
CATCTTCTGC AATCGCAGTC CGCGCGT      SEQ. ID. NO. 50

CAAAAGCTGA GATGAAACAG TGTAAGT      SEQ. ID. NO. 51

GTTTGGTTAA CCAGAAGCCC ATCGT        SEQ. ID. NO. 52

GATGGGCTTC TGGTTAACCA AACT         SEQ. ID. NO. 53
``` whose SEQ. ID. NO. 50 and NO. 51 are on pair of primers and SEQ. ID. NO. 52 and SEQ. ID. NO. 53 are a second pair. The results of these analyses are shown in Table 2.

TABLE 2

Germ-line (VHL) and somatic (sporadic RCC) mutations in the VHL candidate gene.

| Patients | Mutation | Consequence |
|---|---|---|
| VHL family: | | |
| "VA" | 8 bp (TTGTCCGT) insertion after NT714* | frameshift |
| "E" | 9 bp in-frame deletion (NT456–464) | Three amino acid (153–154) deletion (Arg Val Val) |
| "CS" | 3 bp in-frame deletion (NT434–436) | One amino acid deletion (146, Ile) |
| Sporadic RCC | | |
| "UOK118" | 1 bp deletion (NT737) | frameshift |
| "UMRC5" | 1 bp deletion (NT737) | frameshift |
| "UMRC6" | 10 bp deletion (NT715–724) | frameshift |

TABLE 2-continued

Germ-line (VHL) and somatic (sporadic RCC) mutations in the VHL candidate gene.

| Patients | Mutation | Consequence |
|---|---|---|
| "A498" | 5 bp deletion (NT638–642) | frameshift |
| "UOK151" | nonsense C → A (NT761) transversion | stop codon |

*NT = nucleotide(s).

RCC were chosen because according to Knudson's dictum (Knudson (1971)), sporadic cancers should be associated with mutations in the same loci affected in the hereditary form of the same malignancy. So far aberrant patterns have been identified in five RCC cell lines and proved four of them have been proven to be small (1 to 10 bp) deletions creating frameshift mutations and truncated proteins (TABLE 2). The cell lines UMRC5 and RCC "UOK118" have the same 1 bp deletion at nucleotide 737, amino acid 246, creating 28 new amino acids followed by a stop codon. Incidentally, this deletion creates a new EcoRI site, leading to two aberrant bands on Southern blots (not shown). Line UMRC6 has a 10 bp deletion (nucleotides 715 to 724) creating a frameshift such that 32 new amino acids are present followed by a new stop codon. Finally, line A498 has a 5 bp deletion (nucleotides 638 to 642) leading to a premature stop after new 62 amino acids. In the fifth RCC cell line, UOK151, the change is a nonsense (stop codon) mutation resulting from a C to A transversion at nucleotide 761 (TCG→TAG), creating a truncated protein. These data suggest that the VHL disease gene plays an important role in sporadic kidney cancer. As such, RT-PCR or PCR-SSCP as described in this application can be used as diagnostic methods to distinguish primary kidney tumors from tumors that spread to the kidney from other tissues or organs and to distinguish different histological types of kidney tumors.

In the DNA of the VHL lymphoblastioid cell lines derived from VHL patients, SSCP aberrant patterns segregating with the disease were also detected using primers shown in SEQ. ID. NO. 7 thru SEQ. ID. NO. 12. One (patient "VA") was found to be an 8 bp (TTGTCCGT) insertion after nucleotide 714. This insertion created a shift in the reading frame and a truncated protein. The second patient ("CS") had an in-frame 3 bp deletions leading to the removal of amino acid 146 (isoleucine). Finally, patient "E" had an in-frame 9 bp deletion (nucleotides 456 to 464) that resulted in the removal of three amino acids (Arg Val Val) at position 153–155. These combined results strongly support the conclusion that the g7 gene represents the VHL and the sporadic RCC tumor suppressor gene.

EXAMPLE 7

Conservation of the g7 cDNA Across Species

In order to determine whether the g7 cDNA is highly conserved across species ranging from mammals to Drosophila and sea urchins, Zoo blotting using g7 cDNA as a probe was performed on DNA isolated from human (*Homo sapiens*), chimpanzee (*Pan troglodytes*), macaque (*Macaca fascicularis*), cow (*Bovis domesticus*), rat (*Rattus norvigicus*), mouse (*Mus musculus*), chicken (*Gallus domesticus*), frog (*Xenopus laevis*), fly (*Drosophila melanogaster*), sea urchin (*Strongylocentrotus purpuratus*), and yeast (*Saccharomyces ceriviseae*), all purchased from BIOS Laboratories (New Haven, Conn., USA). (Pre) Hybridization was done in Church buffer [G. M. Church and W. Gilbert, *Proc. Natl. Acad. Sci. U.S.A.*, 81, 1991 (1984)] at 65° C. for 18 hours. Blots were washed in 0.1×Church buffer at 60° C. for 60 min. The results of the zoo blot are shown in FIG. 6. The results demonstrate an extensive evolutionary conservation which is indicative of g7 serving a basic life function and also, of g7 having a tumor supressor role.

EXAMPLE 8

Identification and Characterization of the Promoter of the Human VHL Tumor Supressor Gene Transcription initiation sites were located near the putative SPI/AP2 binding site. In one stably transfected clone of the renal carcinoma UMRC 6 cell line, the level of transcription from VHL minigene, containing 5' flanking genomic DNA up to residue −647, was comparable with endogenous VHL expression. Using luciferase reporter constructs which include 5' flanking genomic sequence (residues −467/+195) the minimal promoter was delineated within 106 bp (positions −83/+23) in human embryonic kidney 293 cells. The 5' flanking DNA (residues −467/+195) were also examined for putative transcription factor binding sites and for other regulatory sequences. Several putative binding sequences for tissue specific transcription factors were located near transcription initiation sites. Among them is a core sequence for the Pax family of transcription factors which, apparently, regulates organogenesis. Pax 2 protein, a member of this family, is required for mesenchyme-to-epithelium conversion and is temporarily expressed during kidney development (Rothenpieler and Dressler, 1993). Since clear renal carcinomas originate from proximal tubular epithelium, Pax 2 may have an effect on VHL expression. A related gene, Pax 8, is also activated in developing kidney (Plachov, et al. 1990). Another potentially important site is a 12 bp consensus sequence for the nuclear respiratory factor 1 (NRF-1), which is involved in nuclear-mitochondrial interactions, and apparently, coordinates regulation of nuclear and mitochondrial genes during organelle biogensis (Evans and Scarpulla. 1990; Virbasius and Scarpulla 1994). Identical potential binding sites were also found in several other groups of genes (Virbasius, et al. 1993), including those involved in regulation of the cell cycle (cdc 2, RCC 1) cell growth (ornithine decarboxylase, DNA polymerase alpha) and apoptosis (bcl 2).

Consistently, all observed VHL point mutations were located downstream of the first (−68) methionine codon (Latif, et al., 1993b; Crossey, et al., 1994; Gnarra, et al. 1994; Richards, et al. 1994; Shuin, et al. 1994; Brauch, et al. 1995; Chen, et al. 1995) The codons upstream of this point are rarely used in human translated sequences (Wada, et al. 1992), whereas the downstream codons are used frequently. Finally, the region of homology between the human VHL cDNA and its recently isolated mouse counterpart does not extend upstream of the first methionine (Latif and Duh. personal communication accession No. U12570).

To position the cloned cDNA within the full length VHL mRNA, RNase H mapping was employed (Berger, 1987). Restricted cleavage of the VHL mRNA with RNase H was directed by antisense DNA oligomers (FIGS. 7A–7C). The oligomers 1 and 2 were designed to anneal with the VHL mRNA at 267 to 296 nt and 572 to 596 nt downstream of the cDNA 5' end respectively (FIGS. 7A–7C). As shown on FIG. 7A, the cleaved 5' part of the VHL mRNA is comparable by length with the known cDNA sequence. The size difference between 5' fragments obtained when RNA was digested with different oligomers agrees with the distance calculated from the cDNA sequence. Similar results were obtained using total RNA from 293, UMRCG, U2020 cell lines and human prostate poly(A)—RNA. Thus, the group 7 cDNA completely (or almost completely) represents the 5' end of the VHL mRNA.

In agreement with these data, extensive screening of 155 cDNA libraries (totalling 15 million clones. 100 positive clones were evaluated) and the rapid amplification of 5' cDNA end (5' RACE) technique did not yield any gain upstream of the known cloned cDNA sequences. No gross genomic rearrangements were found within the region covering 60 kb upstream of the VHL cDNA in more than 100 of the VHL kindred. When hybridized to Northern blots, the cloned genomic fragments from this region did not reveal any message the length of VHL.

Mapping of the Transcription Initiation Sites

Attempts to use primer extension to determine the VHL transcription starts were unsuccessful apparently because of high GC content and stable secondary structures near the 5' end of the VHL mRNA.

Thus, the transcription start sites were determined by RNase protection analysis. An antisense riboprobe no. 1 (FIG. 8A) was generated from PstI-NotI (530 nt) genomic fragment, which included a part of exon 1 from the cDNA sequence (223 nt) and the immediate 5' flanking region (308 nt). After hybridization with poly(A)⁻RNA from 293 cells several protected fragments 225 to 240 nt were found (FIG. 8B slots 1, 2 and 3). This result roughly agrees with the RNase H mapping data but it falls far below the predicted figure (390 nt) for the "extended" exon 1 which would presumably contain the whole open reading frame, deducted from genomic sequence downstream of the putative splice acceptor site (Latif, et al., 1993b) . To exclude any artifacts resulting from possible internal RNase cleavage of longer protected fragments, the experiment was repeated with probes no. 2 and no. 3. Probe no. 2, which was identical to probe no. 1 except for a shorter 5' flanking genomic region (44 nt instead of 308 nt) did not reveal any protected fragments (FIG. 8B, slots 7, 8 and 9). The same results were obtained with poly(A)⁻RNA from human prostate and adult kidney (data not shown). According to these data transcription start sites were placed not more than 30 nt upstream of the 5' cloned cDNA 5' border.

For precise mapping of the transcription start sites, a shorter probe (no. 5; FIG. 8A) was used which included 149 nt of the exon 1 sequences from the cDNA and 104 nt of the 5' flanking genomic region. Using RNA markers, the size of the protected fragments was identified as 152, 153, 161, 162, 163, 171 and 176 nts, which means that the 5' ends of the VHL mRNA were located respectively 3, 4, 12, 13, 14, 22 and 27 bp upstream of the cDNA border. The first nucleotide of the RNA specie which was initiated 22 bp upstream of the cDNA border was assigned number +1 (FIG. 8C).

A Functional Promoter is Located Around Initiation Sites

To test the promoter activity a fragment from the 5' flanking genomic region (bases −467 through −195) was inserted into pGL-2-enhancer luciferase reporter vector, which was transfected into 293 cells. The fragment was shown to drive transcription of luciferase. The efficiency of the full length VHL promoter (bases −467–195) in 293 cells was assigned 100% SV 40 early promoter activity comprised 60% and thymidine kinase promoter—about 500 % of the full VHL promoter strength. The promoter activity appeared to be unidirectional, since the activity of the fragment in reverse orientation was about seven times weaker.

To localize more precisely the minimal promoter region, a set of 5' and 3' deletion constructs was prepared (FIG. 9). The results of transfection indicated that the minimal promoter can be delineated within 106 bp, between restriction sites for EagI (−83) and SacII (−23). The minimal construct retained 32±9% of the full promoter activity. No separate promoter activity was found upstream of the EagI site (−83/−467). The region downstream of the SmaI site (+30/+195) enhances transcription by about two times; however it does not possess promoter activity of its own.

Because the mutations in the VHL gene apparently play a critical role in the origin of clear renal carcinoma (Latif, et al., 1993b; Gnarra et al. 1994; Shuin et al. 1994), the UMRC 6 cell line derived from this malignancy was also studied. When normalized to β-galactosidase expressed under cytomegalovirus (CMV) promoter, the luciferase activity in UMRC 6 cells was about two times lower than in 293 cells. However, the relative activity of different constructs compared to the full length construct no. 1 (FIG. 3) in each cell line appeared to be similar. These data indicate that the same promoter region is active in both 293 and UMRC6 cell lines.

5' Flanking Genomic Fragment, Containing VHL Promoter. Confers Apparently Normal Level of Transcription to VHL Minigene To estimate the level of transcription from the native VHL promoter in VHL minigenes in renal carcinoma, three minigene constructs were used, which were based on the pRc/CMV vector (Invitrogen). In these constructs CMV promoter/enhancer region was substituted by a VHL 5' flanking EcoRI-NotI genomic fragment which was fused to the rest of the VHL cDNA (FIG. 10A). The final expression plasmids included VHL sequences from base −647 to +710 (pRcpVHL) and from −647 to +1664 (pRcpVHL3U). To eliminate any possible effects of the native VHL protein on cell growth, a frameshift was introduced into the VHL reading frame (duplication of bases −408/−412 in exon 2) of the pRcpVHL by digestion with Baste, fill-in with Klenow fragment and relegation (plasmid pRcpVHLm). A transcript from the construct containing CMV promoter and VHL reading time (pRc-HAVHL) was used as a size marker of Northern blots. For transfection, the UMRC6 cell line was used. The cells were shown to have a 10 bp microdeletion in VHL exon 3 (Latif et al., 1993b) which would allow discrimination between endogenous and exogenous VHL mRNA by reverse transcription/polymerase chain reaction (RT-PCR). After transfection 40 to 50 geneticin positive clones were pooled and expression from VHL minigenes was assayed by Northern analyses (FIG. 10B) and RT-PCR. The sizes of the exogenous VHL mRNAs indicated that transcription was initiated roughly from the same region inside the NotI-EcoRI fragment as we have shown above for endogenous VHL gene using the RNase protection assay. RT-PCR analysis confirmed expression from the VHL minigenes.

The question of whether the obvious difference in the level of expression between endo- and exogenes (FIG. 10B) reflected a lack of important regulatory elements within the minigenes or just frequent rearrangements of the VHL transgene in many of the geneticin resistant clones was next investigated. Five colonies were expanded and analysed by Southern and Northern blotting analyses (three of them were transfected by pRcpVHL3U construct, another two carried pRcpVHLm). However, only one clone (pRcpVHLm, clone 4) was shown to have nonrearranged VHL transgene (1.3 kb EcoRI fragment, FIG. 11A) which expressed VHL mRNA (FIG. 11B). Both the 950 nt and about 4800 nt transcripts showed a similar signal intensity on Northern blot with apparently the same gene copy number on Southern blot. This observation may indicate that the 5' VHL genomic region confers apparently normal level of transcription in the UMRC 6 renal carcinoma cell line. However, other factors may interfere, for example, the enhancing, (silencing) activity of the DNA sequences near integration site and different stability of the exogenous mRNA due to absence of a full-length 3' UTR.

Sequence Analysis of the VHL Promoter

The VHL promoter and exon 1 comprised a CpG island. The GC content within the minimal promoter region (−83/−23) is 72.6%. The minimal promoter harbors several GC-specific restriction sites including one for EagI, three for BssHII, one for SalI and six for HhaI. The region around minimal promoter (−467/−195) does not contain TATA (SEQ ID NO:58) and CCAAT (SEQ ID NO:59) boxes. A putative binding suite for SP-1 (KRGGCGKRRY; −1–13; Briggs, et al., 1986) and AP-2 transcription factors (YCSCCMNSS(SEQ ID NO60): −4/+13; Imagawa, et al. 1987) was found near transcription initiation sites. It appears to play a major role in the VHL transcription initiation. However, the reporter deletion analysis described above indicates that the region −83–10 is also functionally essential. Another site for SP1/AP2 was found in position +74/−83. Two sites for SP1 with a more loose recognition sequence (KRGGCKRRK(SEQ ID NO:61); Faisst and Meyer, 1992) and one site for AP2 factor were located upstream of the minimal promoter (FIG. 6). Other putative transcription factor binding sites include Pax core sequence (GTTCC(SEQ ID NO:62); −56/−60; Chaiepakis, et al., 1991) sites for nuclear respiratory factor 1 (YGCGCAYGCGCR(SEQ ID NO57): −92/−103; Evans and Scarpulla, 1990), nuclear hormone receptor for retinoic acid H-2RIIBP (GAGCTC(SEQ ID NO:63); −21/−26; −293/−298; Marks, et al., 1992) and several other factors.

An important feature of the region further upstream to the VHL minimal promoter is a termination polyadenylation signal for RNA polymerase II (−384/−379), which may prevent continuous transcription form other putative promoters upstream. Indeed, no evidence of such promoters has been found as yet.

The contents of all citations, i.e., journal articles, patents and the like, are incorporated herein by reference.

It is understood that the examples and embodiments described herein are for illustrative purposes and that various modifications and changes in light thereof to persons skilled in the art are included within the spirit and purview of this application and scope of the appended claims.

The present invention further provides for the following nucleic acid promoter sequence of the wild-type VHL disease gene, designated SEQ. ID. NO: 6:

```
AGAGGCCAAG GCAGGAGGAT CACTTGAACC CAGGAGTTCG        40

AGACCAGCCT AGGCAACATA GCGAGACTCC GTTTCAAACA        80

ACAAATAAAA ATAATTAGTC GGGCATGGTG GTGCGCGCCT       120

ACAGTACCAA CTACTCGGGA GGCTGAGGCG AGACGATCGC       160

TTGAGCCAGG GAGGTCAAGG CTGCAGTGAG CCAAGCTCGC       200

GCCACTGCAC TCCAGCCCGG GCGACAGAGT GAGACCCTGT       240

CTCCAAAAAA AAAAAAAAAC ACCAAACCTT AGAGGGGTGA       280

AAAAAAATTT TATAGTGGAA ATACAGTAAC GAGTTGGCCT       320

AGCCTCGCCT CCGTTACAAC AGCCTACGGT GCTGGAGGAT       360

CCTTCTGCGC ACGCGCACAG CCTCCGGCCG GCTATTTCCG       400

CGAGCGCGTT CCATCCTCTA CCGAGCGCGC GCGAAGACTA       440

CGGAGGTCGA CTCGGGAGCG CGCACGCAGC TCCGCCCCGC       480

GTCCGACCCG CGGATCCCGC GGCGTCCGGC CCGGGTGGTC       520

TGGATCGCGG AGGGAATGCC CCGGAGGGCG GAGAACTGGG       560

ACGAGGCCGA GGTAGGCGCG GAGGAGGCAG GCGTCGAAGA       600

GTACGGCCCT GAAGAAGACG GCGGGGAGGA GTCGGGCGCC       640

GAGGAGTCCG GCCCGGAAGA GTC                         663
```

Variations are contemplated in the cDNA sequence shown in SEQ. ID. NO: 1 which will result in a DNA sequence that is capable of directing production of analogs of the VHL protein shown in SEQ. ID. NO: 2. It should be noted that the DNA sequences set forth herein represent preferred embodiments of the present invention. Due to the degeneracy of the genetic code, it is to be understood that numerous choices of nucleotides may be made that will lead to a DNA sequence capable of directing production of the instant VHL protein or its analogs. As such, DNA sequences which are functionally equivalent to the sequences set forth herein or which are functionally equivalent to sequences that would direct production of analogs of the VHL protein produced pursuant to the amino acid sequence set forth above, are intended to be encompassed within the present invention.

The term analog includes any polypeptide having an amino acid residue sequence substantially identical to a sequence specifically shown herein in which one or more residues have been conservatively substituted with a functionally similar residue and which displays the function of the VHL protein as described herein. Examples of conservative substitutions include the substitution of non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that the resulting protein or polypeptide displays the requisite functional activity.

"Chemical derivative" refers to a VHL protein or polypeptide having one or more residues chemically derivatized by reaction of a functional side group. Examples of such derivatized molecules include, but are not limited to, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. A VHL protein or polypeptide of the present invention also includes any protein or polypeptide having one or more additions and/or deletions or residues relative to the sequence of a polypeptide whose sequence is shown herein, so long as the requisite activity is maintained.

The present invention also relates to methods for detecting carriers of the VHL gene.

It is understood by one skilled in the art that the methods for detection disclosed in the present invention can be used prenatally to screen a fetus or presymptomatically to screen a subject at risk through his/her family history. In addition, these methods can be used to determine the involvement of the VHL gene in other human malignancies such as sporadic renal cancer, uterine cancer, breast cancer, testicular cancer, bladder cancer, pancreatic cancer, ovarian cancer and lung cancer.

Specifically, the methods of the present invention may be used to detect familial types of renal cell carcinoma. Examples of familial types of renal cell carcinoma include, but are not limited to, hereditary, nonpappillary renal cell carcinoma; VHL disease; and hereditary papillary RCC.

Additionally, the methods of the present invention may be used to detect sporadic, noninherited malignancies, such as, for example, renal cell carcinoma.

In one embodiment of the invention, the method for detecting carriers of the VHL gene comprises analyzing the DNA of a subject for mutations of the VHL gene associated with VHL disease, or diseases related thereto.

For purposes of the present invention, subject means a mammal and mutation means inversion, translocation, insertion, deletion or point mutation of the VHL gene.

For analysis of the DNA, a biological specimen is obtained from the subject. Examples of biological specimens that may be analyzed by the methods of the present invention include, but are not limited to, tissue biopsies, whole blood, serum, urine, feces, cerebrospinal fluid or other samples normally tested in the diagnosis of disease. Preferred biological specimens are whole blood or urine.

Although it is not always required, it is preferable to at least partially purify DNA from the biological specimen prior to analysis. For example, after disruption of cells in the specimen, nucleic acid can be extracted from contaminating cell debris and other protein substances by extraction of the sample with phenol. In phenol extraction, the aqueous sample is mixed with an approximately equal volume of redistilled phenol and centrifuged to separate the two phases. The aqueous phase containing the nucleic acid is removed and precipitated with ethanol to yield nucleic acid free of phenol. Alternatively, DNA can be purified from the biological sample according to Sidransky, D. et al. (Science (1992) 256:102–105; Science (1991) 252:706) or by the method of Glenn, et al. (Glenn, G.M. et al. JAMA (1992) 267:1226–1231). The DNA to be analyzed can be either single- or double-stranded.

Methods for analyzing the DNA for mutations in the VHL gene include Southern blotting after digestion with the appropriate restriction enzymes (restriction fragment length polymorphism, RFLP) (Botstein, D. Amer. J. Hum. Genet. (1980) 69:201–205), denaturing gradient electrophoresis technique (Myers, R. M., Nature (1985) 313:495–498), oligonucleotide hybridization (Conner, R. et al., EMBO J. (1984) 3:13321–1326), RNase digestion of a duplex between a probe RNA and the target DNA (Winter, E. et al., Proc. Natl. Acad. Sci. U.S.A. (1985) 82:7575–7579), polymerase chain reaction (PCR) (Saiki, P. K. et al., Science (1988) 239:487–491; U.S. Pat. Nos. 4,683,195 and 4,683, 202), ligase chain reaction (LCR) (European Patent Application Nos. 0,320,308 and 0,439,182), and PCR-single stranded conformation analysis (PCR-SSCP) (Orita, M. et al., Genomics (1989) 5:874–879; Dean, M. et al. Cell (1990) 61:863–871). In one preferred embodiment, DNA is analyzed by Southern analysis.

The DNA to be analyzed via Southern analysis is digested with one or more restriction enzymes. The restriction enzymes to be used in the present invention are those enzymes for whom the presence or absence of their recognition site is linked to a disease, including, but not limited to, VHL disease and sporadic renal carcinoma. Preferred restriction enzymes include EcoRI, HindIII, PstI, DraI, BamHI, BglI, BglII, and PvuII. Following restriction digestion, resultant DNA fragments are separated by gel electrophoresis and the fragments are detected by hybridization with a labelled nucleic acid probe (Southern, E. M. J. Mol. Biol. (1975) 98:503–517).

The nucleic acid sequence used as a probe in Southern analysis can be labeled in single-stranded or double-stranded form. Labelling of the nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, N.Y.). In addition, there are known non-radioactive techniques for signal amplification including methods for attaching chemical moieties to pyrimidine and purine rings (Dale, R. N. K. et al. (1973) Proc. Natl. Acad. Sci., 70:2238–2242; Heck, R. F. 1968) S. Am. Chem. Soc., 90:5518–5523), methods which allow detection by chemiluminescence (Barton, S. K. et al. (1992) J. Am. Chem. Soc., 114:8736–8740) and methods utilizing biotinylated nucleic acid probes (Johnson, T. K. et al. (1983) Anal. Biochem., 133:126–131; Erickson, P. F. et al. (1982) J. of Immunology Methods, 51:241–249; Matthaei, F. S. et al. (1986) Anal. Biochem., 157:123–128) and methods which allow detection by fluorescence using commercially available products. The size of the probe can range from about 200 nucleotides to about several kilobases. A preferred probe size is about 500 to about 2000 nucleotides. Each of the nucleic acid sequences used as a probe in Southern analysis is substantially homologous to the corresponding portion of the cDNA sequence shown in SEQ ID NO: 1. By "substantially homologous" is meant a level of homology between the nucleic acid sequence used as a probe and the corresponding sequences shown in SEQ. ID. NO: 1 and SEQ. ID. NOS: 3–6. Preferably, the level of homology is in excess of 70%, most preferably in excess of 80%, with a particularly preferred nucleic acid sequence being in excess of 90% homologous with the sequences shown in SEQ. ID. NO: 1 and SEQ. ID. NOS: 3–6.

Once the separated DNA fragments are hybridized to the labelled nucleic acid probes, the restriction digest pattern can be visualized by autoradiography and examined for the presence or absence of a restriction fragment length polymorphism (RFLP) associated with VHL disease, or diseases related thereto.

In a second preferred embodiment, the DNA is analyzed for mutations in the VHL gene by PCR-SSCP (Orita et al., (1989), Dean et al., (1990)). In this method, each of the pairs of primers selected for use in PCR are designed to hybridize with sequences in the VHL gene which are an appropriate distance apart (at least about 50 nucleotides) in the gene to permit amplification and subsequent detection of mutations in the amplification product. Primer pairs which can specifically hybridize to such VHL gene sequences can be derived from the VHL gene sequence.

In a preferred embodiment, the primers are derived from the cDNA sequences shown in SEQ. ID. NO: 1 and SEQ. ID. NOS: 3–6. Each primer of a pair is a single-stranded oligonucleotide of about 15 to about 50 bases in length which is complementary to a sequence at the 3' end of one of the strands of a double-stranded target sequence. Each pair comprises two such primers, one of which is complementary to the 3' end and the other of which is complementary to the other 5' end of the target sequence. The target sequence is generally about 100 to about 300 base pairs long but can be as large as 500–600 base pairs. Optimization of the amplification reaction to obtain sufficiently specific hybridization to the VHL gene is well within the skill in the art and is preferably achieved by adjusting the annealing temperature.

The present invention also provides purified and isolated pairs of primers for use in analysis of DNA for mutations in the VHL disease gene. The nucleic acid sequences of the primers are set forth below as SEQ. ID. NOS: 7–12.

```
                                                SEQ. ID. NO: 7
ATAGTGGAAA TACAGTAACG AGTTGGCCTA GCCTCGC

SEQ. ID. NO: 8
CCCAGCTGGG TCGGGCCTAA GCGCCGGGCC CGT

SEQ. ID. NO: 9
GTGGCTCTTT AACAACCTTT GCTTGTCCCG ATA

SEQ. ID. NO: 10
CAAGTGGTCT ATCCTGTACT TACCACAACA CCT

SEQ. ID. NO: 11
TGTATACTCT GAAAGAGCGA TGCCTCCAGG T

SEQ. ID. NO: 12
TACCATCAAA AGCTGAGATG AAACAGTGTA AGT
``` where SEQ ID NO: 7 and SEQ ID NO: 8 represent one pair of primers; SEQ ID NO: 9 and SEQ ID NO: 10 represent a second pair of primers and SEQ ID NO: 11 and SEQ ID NO: 12 represent a third pair of primers.

Additional primers provided by the present invention for use in analysis of DNA for mutations in the VHL disease gene include the following primers, set forth as SEQ. ID. NOS: 13–22:

```
                                                SEQ. ID. NO: 13
AGTGGAAATA CAGTAACGAG TTGGCCT

SEQ. ID. NO: 14
GAAATACAGT AACGAGTTGG CCTAGC
```

-continued

GTCCCAGTTC TCCGCCCTCC GGGGCAT                SEQ. ID. NO: 15

TGGGTCGGGC CTAAGCGCCG GGCCCGT                SEQ. ID. NO: 16

CTTTAACAAC CTTTGCTTGT CCCGATA                SEQ. ID. NO: 17

GTGGCTCTTT AACAACCTTG C                      SEQ. ID. NO: 18

GTCTATCCTG TACTTACCAC AACACCT                SEQ. ID. NO: 19

CCTGTACTTA CCACAACACC TTAT                   SEQ. ID. NO: 20

CTGAGACCCT AGTCTGCCAC TGAGGAT                SEQ. ID. NO: 21

TTCCTTGTAC TGAGACCCTA GT                     SEQ. ID. NO: 22

GGAAATACAGT AACGAGTTGG CCT                   SEQ. ID. NO: 23

GGAAATACAG TAACGAGTTG GCCTAGC                SEQ. ID. NO: 24

ACGGGCCCGG CGCTTAGGCC CGACCCA                SEQ. ID. NO: 25

ACGGGCCCGG CGCTTAGGCC CGACCCAGCA GG          SEQ. ID. NO: 26

GTGGCTCTTT AACAACCTTT GCTTGTCCCG ATA         SEQ. ID. NO: 27

CTTTAACAAC CTTTGC                            SEQ. ID. NO: 28

GATAAGGTTG TTGTGGTAAG TACAGGA                SEQ. ID. NO: 29

AGGTTGTTGT GGTAAGTACA GGATAGC                SEQ. ID. NO: 30

CTCCTTGTAC TGAGACCCTA GT                     SEQ. ID. NO: 31

GTGAGACCCT AGTCTGCCAC TGAGGAT                SEQ. ID. NO: 32

Examples of primers useful in the present invention which may be used to hybridize to mutant forms of the VHL gene include, but are not limited to, primers that possess the following mutated sequences:
(1) GAGGTCAC (SEQ. ID. NO. 33)
A mutation from the nucleotide sequence GATAGGT-CAC to GAGGTCAC in the VHL gene results in the loss of the exon 2 splice acceptor and the loss of expression of exon 2.
(2) GATTGGTCAC (SEQ. ID. NO. 34)
A mutation from the nucleotide sequence GATAGGT-CAC to GATTGGTCAC in the VHL gene results in the loss of the exon 2 splice acceptor.
(3) A mutation from G to A at nucleotide 676 of SEQ. ID. NO: 1 and an eight nucleotide deletion of GTACTGAC.
A VHL gene possessing these mutations results in the loss of the exon 2 splice donor.

The primers of this invention can be synthesized using any of the known methods of oligonucleotide synthesis (e.g., the phosphodiester method of Agarwal et al. 1972. Agnew. Chem. Int. Ed. Engl. 11:451, the phosphotriester method of Hsiung et al. 1979. Nucleic Acids Res. 6:1371, or the automated diethylphosphoramidite method of Beuacage et al. 1981. Tetrahedron Letters 22:1859–1862), or they can be isolated fragments of naturally occurring or cloned DNA. In addition, those skilled in the art would be aware that oligonucleotides can be synthesized by automated instruments sold by a variety of manufacturers or can be commercially custom ordered and prepared. In one embodiment, the primers can be derivatized to include a detectable label suitable for detecting and/or identifying the primer extension products (e.g., biotin, avidin, or radiolabeled dNTP's), or with a substance which aids in the isolation of the products of amplification (e.g. biotin or avidin). In a preferred embodiment, SEQ. ID. NO: 7 through SEQ. ID. NO: 34 are synthetic oligonucleotides.

In an alternative embodiment, primer pairs can be selected to hybridize to mutant forms of the VHL gene. The selected primer pairs will hybridize sufficiently specifically to the mutated gene sequences such that non-specific hybridization to VHL gene sequences will not prevent identification of the amplification product of the mutant gene sequence. Primer pairs which hybridize to mutations in the VHL gene sequence can be used to amplify specific mutant gene sequences present in the DNA of a biological sample.

The amplification products of PCR can be detected either directly or indirectly. In the PCR-SSCP method, direct detection of the amplification products is carried out via labelling of primer pairs. Labels suitable for labelling the primers of the present invention are known to one skilled in the art and include radioactive labels, biotin, avidin, enzymes and fluorescent molecules. The derived labels can be incorporated into the primers prior to performing the amplification reaction. A preferred labelling procedure utilizes radiolabeled ATP and T4 polynucleotide kinase (Sambrook, J. et al. (1989) in "Molecular Cloning, A Laboratory Manual", Cold Spring Harbor Press, Plainview, N.Y.). Alternatively, the desired label can be incorporated into the primer extension products during the amplification reaction in the form of one or more labelled dNTPs. In the present invention, the labelled amplified PCR products can be analyzed for mutations of the VHL gene associated with VHL disease gene, or diseases related thereto, via separating the PCR products by denaturing polyacrylamide gel electrophoresis or via direct sequencing of the PCR-products.

In yet another embodiment, unlabelled amplification products can be analyzed for mutations in the VHL gene via hybridization with nucleic acid probes radioactively labelled or labelled with biotin, in Southern blots or dot blots. Nucleic acid probes useful in the embodiment are those described previously for Southern analysis.

In a second embodiment, the method for detecting carriers of the VHL gene comprises analyzing the RNA of a subject for mutations or alterations in VHL-specific mRNA associated with VHL disease and diseases related thereto, including, but not limited to, sporadic renal cancer, uterine cancer, breast cancer, testicular cancer, bladder cancer, pancreatic cancer, ovarian cancer and lung cancer.

For the analysis of RNA by this method, RNA derived from blood or a tumor biopsy sample is obtained from said subject where said tumors include, but are not limited to, tumors of the eye, brain, liver, kidney, pancreas, and pheochromocytomas.

The RNA to be analyzed can be isolated from blood or tumor biopsy samples as whole cell RNA or as poly(A)$^+$ RNA. Whole cell RNA can be isolated by methods known to those skilled in the art. Such methods include extraction of RNA by differential precipitation (Birnbiom, H. C. (1988) Nucleic Acids Res., 16:1487–1497), extraction of RNA by organic solvents (Chomczynski, P. et al. (1987) Anal. Biochem., 162:156–159) and extraction of RNA with strong denaturants (Chirgwin, J. M. et al. (1979) Biochemistry, 18:5294–5299). Poly(A)+RNA can be selected from whole cell RNA by affinity chromatography on oligo-d(T) columns (Aviv, H. et al. (1972) Proc. Natl. Acad. Sci., 69:1408–1412). A preferred method of isolating RNA is extraction of whole cell RNA by acid-phenol (Chomczynski et al. 1987).

The methods for analyzing the RNA for alterations in the pattern or level of VHL specific mRNA expression linked to VHL disease and diseases related thereto, include Northern blotting (Alwine, J. C. et al. (1977) Proc. Natl.

Acad. Sci., 74:5350–5354), dot and slot hybridization (Kafatos, F. C. et al. (1979) Nucleic Acids Res., 7:1541–1522), filter hybridization (Hollander, M. C. et al. (1990) Biotechniques; 9:174–179), RNase protection (Sambrook, J. et al. (1989) in "Molecular Cloning, A Laboratory Manual", Cold Spring Harbor Press, Plainview, N.Y.) and reverse-transcription polymerase chain reaction (RT-PCR) (Watson, J. D. et al. (1992) in "Recombinant DNA" Second Edition, W. H. Freeman and Company, New York). One preferred method is Northern blotting.

The nucleic acid sequence used as a probe for detecting VHL-specific mRNA expression is substantially homologous to SEQ. ID. NO: 1. By "substantially homologous" is meant a level of homology between the nucleic acid sequence and the cDNA sequence of SEQ. ID. NO: 1. Preferably, the level of homology is in excess of 70%, more preferably in excess on 80%, with a particularly preferred nucleic acid sequence being in excess of 90% homologous with the cDNA sequence shown in SEQ. ID. NO: 1.

A most preferred method is reverse transcription-polymerase chain reaction (RT-PCR) where the primers used to amplify the cDNA produced via reverse transcription of RNA are derived from the cDNA sequence shown in SEQ. ID. NO: 1. These primers can be labelled as described earlier and the RT-PCR products can be analyzed for mutations of the VHL gene associated with VHL disease, or diseases related thereto, via denaturing polyacrylamide gel electrophoresis of the RT-PCR products or via direct sequencing of the RT-PCR products.

In a third embodiment, the method for detecting carriers of the VHL gene comprises analyzing the DNA of a subject for mutations or alterations in VHL-specific DNA associated with VHL disease, or diseases related thereto, such as sporadic renal cancer, uterine cancer, breast cancer, testicular cancer, bladder cancer, pancreatic cancer, ovarian cancer and lung cancer.

The present invention also encompasses recombinant proteins derived from the cDNA shown in SEQ. ID. NO: 1 and antibodies directed to said proteins (called VHL proteins). Recombinant VHL proteins can be produced by recombinant DNA methodology known to one skilled in the art. For example, a nucleic acid sequence capable of encoding a protein comprising all or part of the amino acid sequence shown in SEQ. ID. NO: 2 can be cloned into a vector capable of being transferred into, and replicated in, a host organism. A suitable nucleic acid sequence for the purpose of this invention are the sequences shown in SEQ. ID. NO: 1 and SEQ. ID. NOS: 3–6. Suitable expression vectors include, but are not limited to, vaccinia virus vectors, baculovirus vectors, and *E. coli* pTRCHIS (Invitrogen Co. San Diego). The recombinant expression vector produced by inserting a nucleic acid sequence capable of directing synthesis of VHL protein in a suitable expression vector can be transfected into *E. coli* or into suitable eukaryotic cell systems by methods known to one skilled in the art.

Cells containing the expressed recombinant VHL protein, cell lysate from cells transfected with a recombinant expression vector or a culture supernatant containing the expressed VHL protein can be used as an immunogen to elicit production of anti-VHL antibodies in a mammal. Alternatively, one can generate synthetic peptides for use as immunogens from the amino acid sequence shown in SEQ. ID. NO: 2. Preferred synthetic peptide sequences for use as immunogens are shown below:

SEQ ID NO. 35:
Glu Glu Tyr Gly Pro Glu Glu Asp Gly Gly Glu Glu Ser Gly
SEQ ID NO. 36:
Gly Thr Gly Arg Arg Ile His Ser Tyr Arg Gly His Leu

While it is possible for the immunogen to be administered to the mammal in pure or substantially pure form, it is preferable to present it as a pharmaceutical composition, formulation or preparation. Suitable mammals for immunization include mice, rabbits and the like. The anti-VHL antibody of the present invention is typically produced by immunizing a mammal with an immunologically effective amount of synthetic peptide of this invention. The preparation of polyclonal or monoclonal antibodies against such a peptide is well known in the art (Standt, et al. (1988) J. Exp. Med. 157:687–704). The anti-VHL peptide antibody molecules induced by immunization of a mammal with the recombinant VHL protein are then collected from the mammal and those immunospecific for the VHL protein are isolated to the extent desired by well known techniques such as, for example, immunochromatography.

In a third embodiment, the method for detecting carriers of the VHL gene comprises:

analyzing the protein of a subject for alterations in VHL protein expression.

For analysis of protein by this method, protein is obtained from biological specimens such as tumor biopsy samples and urine and the like. The protein can be obtained as a crude lysate or it can be further purified by methods known to one skilled in the art (Sambrook, J. et al. (1989) in "Molecular Cloning, A Laboratory Manual", Cold Spring Harbor press, Plainview, N.Y.).

Crude protein lysate can be analyzed for VHL protein by immunoassays using anti-VHL antibody.

Immunoassays of the present invention may be a radioimmunoassay, Western blot assay, immunofluorescent assay, enzyme immunoassay, chemiluminescent assay, immunohistochemical assay and the like. Standard techniques known in the art for ELISA are described in *Method in Immunodiagnosis*, 2nd Edition, Rose and Bigazzi, eds., John Wiley and Sons, 1980 and Campbell et al., *Methods of Immunology*, W. A. Benjamin, Inc., 1964, both of which are incorporated herein by reference. Such assays may be a direct, indirect, competitive, or noncompetitive immunoassay as described in the art. (Oellerich, M. 1984. *J. Clin. Chem. Clin. BioChem.* 22:895–904).

Detection of the VHL protein anti-VHL antibody complex formed can be accomplished by reaction of the complex with a secondary antibody such as labelled anti-rabbit antibody. The label may be an enzyme which is detected by incubating the complex in the presence of a suitable fluorimetric or calorimetric reagent. Other detectable labels may also be used, such as radiolabels, or colloidal gold, and the like. The labelled VHL protein-anti-VHL antibody complex is then visualized by autoradiography.

The present invention also relates to a method for treating a carrier of the VHL gene in which an expression vector containing a nucleic acid sequence representing the VHL gene is administered to the carrier. Nucleic acid sequences representing the VHL gene are SEQ. ID. NO: 1 and SEQ. ID. NOS: 3–7. Such nucleic acid sequences may be inserted into a suitable expression vector by methods known to those skilled in the art (Example 5). Expression vectors suitable for producing high efficiency gene transfer in vivo include retroviral, adenoviral and vaccinia viral vectors.

Expression vectors containing a nucleic acid sequence representing the VHL gene can be administered intravenously, intramuscularly, subcutaneously, intraperitoneally or orally. A preferred route of administration is intravenously.

The invention also provides a diagnostic kit for detecting carriers of the VHL gene. This diagnostic kit comprises purified and isolated nucleic acid sequences according to SEQ ID. NO: 7 through SEQ ID NO: 34, said sequences useful as PCR primers in analyzing DNA for the presence of mutations of the VHL gene linked to VHL disease, or diseases related thereto.

The invention also provides a diagnostic kit for detecting regulatory defects of the VHL gene. This diagnostic kit comprises purified and isolated nucleic acid sequences according to SEQ. ID. NO: 7 through SEQ. ID. NO: 34, said sequences useful as PCR primers in analyzing DNA for mutations of the VHL gene linked to VHL disease and diseases related thereto, including, but not limited to, sporadic renal cancer, lung cancer, uterine cancer, breast cancer, testicular cancer, ovarian cancer, adrenal tumors, brain tumors, lung tumors or other cancers.

The nucleic acid sequences of the present invention according to SEQ. ID. NO: 7 through SEQ. ID. NO: 34 are useful in the detection of hereditary and sporadic kidney cancers by the detection of abnormalities of the VHL gene in biological samples using the primers of the present invention.

The present invention further provides a method of preventing or treating regulatory defects linked to VHL disease. Specifically, the present invention provides a method of treating or preventing cancer in a subject by contacting the cancer with an amount of the VHL gene of the present invention effective to treat the cancer. This method comprises administration of the VHL gene in an amount effective to prevent or treat regulatory defects associated with VHL disease and diseases related thereto, including, but not limited to, sporadic renal cancer, lung cancer, uterine cancer, breast cancer, testicular cancer and ovarian cancer.

In one embodiment of the invention, the VHL gene sequence or analog thereof is administered in a pharmaceutically acceptable carrier. A pharmaceutically acceptable carrier encompasses any of the standard pharmaceutical carriers such as sterile solution, tablets, coated tablets and capsules. Such carriers may typically contain excipients such as starch, milk, sugar, certain types of clay, gelatin, stensic acid, talc, vegetable fats or olis, gums, glycols, or other known excipients. Such carriers may also include flavor and color additives and other ingredients.

Types of cancer that may be treated using the VHL sequences or proteins of the present invention include, but are not limited to, VHL disease and diseases related thereto, including, but not limited to, sporadic renal cancer, lung cancer, uterine cancer, breast cancer, testicular cancer, ovarian cancer, adrenal tumors, brain tumors, lung tumors or other cancers.

Specific carcinomas which may be treated using the VHL sequences or proteins of the present invention include, but are not limited to, renal cell carcinoma, pheochromocytoma, retinal angioma, hemangioblastoma, pancreatic cysts, pancreatic tumors and epididymal cystadenoma.

Any articles or patents referenced herein are incorporated by reference. The following examples illustrate various aspects of the invention but are in no way intended to limit the scope thereof.

MATERIALS

The subjects analyzed in the following examples were kindred identified by ophthalmologists, urologists, medical geneticists and neurosurgeons in the United States, Europe, and Canada. The members of the families resided in Louisiana, Tennessee, Mississippi, Virginia, Pennsylvania, New York, Michigan, Quebec, Nova Scotia, United Kingdom, and the Netherlands. Medical records of each family member known to be affected were reviewed. Asymptomatic family members and family members in whom there was uncertainty about the diagnosis were examined after informed consent for occult evidence of the illness at the Clinical Center of the National Institutes of Health. The examination consisted of a history and physical examination of the scrotum. An asymptomatic member of a VHL family was considered to be affected if one or more of the following disease manifestations were detected: retinal angioma(s), spinal or cerebellar hemangioblastoma(s), pheochromocytoma(s), multiple pancreatic cysts, and multiple bilateral renal cysts accompanied by renal cell carcinoma. Disease diagnosis was made without knowledge of restriction fragment length polymorphism (RFLP) status.

Restriction enzymes were from Bethesda Research Laboratory (BRL) (Bethesda, Md.), New England Biolabs (Beverly, Mass.) and Boehringer Mannheim (Indianapolis, Ind.) and were used as recommended by the manufacturers. $\delta$-$^{32}$PdCTP (~3000 iu/mmol) was from Amersham (Arlington Heights, Ill.). The various human tissue polyadenylated RNAs used in Northern blotting were purchased from Clontech (Palo Alto, Calif.) as was the adult kidney double-stranded complementary DNA sample. PCR and RT-PCR bits were from Perkin Elmer/Cetus (Norwalk, Conn.); deoxynucleotide triphosphates and flourescently labelled dideoxynucleotides were from Applied Biosystems, Inc. (Foster City, Calif.). Nylon membranes were purchased from MSI, Inc. (Westlore, Mass.).

METHODS

Southern and Northern blottings, filter hybridization and probe labelling were carried out using random priming and were otherwise performed by standard protocols (Sambrook, J. et al. (1989)). DNA inserts were purified following the GeneClean (Bio 101) (BioRad, Richmond, Calif.) protocol and used for subcloning or labelling. Oligonucleotides used as primers in PCR or RT-PCR or for sequencing were synthesized on the Applied Biosystems, Inc. Model 392 DNA/RNA synthesizer, according to the manufacturers recommendations. Pulse field goal electrophoresis was carried out using CHEF-DRII or CHEF mapper XA systems as described by the manufacturer (BioRad) under conditions optimal for obtaining the desired resolution.

PCR—The PCR was performed in a 50 ul reaction volume in a mixture containing luM of each primer, 250 uM of each deoxynucleotide triphosphate, 5 ul of 10×PCR buffer (500MM KC1; 120MM Tris-HCl, pH 8.0; 1.5 MM MgCl$_2$; and 0.1% gelatin) and 1.25 units of AmpTaq (Cetus) DNA polymerase, in a first generation automated thermal cycler (Perkin-Elmer/Cetus). The PCR conditions consisted of 40 cycles of denaturation for one minute at 94° C., annealing for one minute at specified temperatures (55–65° C.) and extension for 4 minutes at 72° C. followed by 7 minutes of final extension of 72° C.

RNA Preparation and Northern Blotting—Total cellular RNA was isolated by extraction of lymphoblastoid cell lines of affected VHL patients or kidney tissues in guanidine thiocyanate followed by centrifugation through a 5.7 M CsCl cushion according to standard protocols (Sambrook, J. et al. (1989)). RNA samples were separated by electrophoresis in 1% agarose gels containing 2.2M formaldehyde, transferred to nylon membranes and hybridized to g7 cDNA probe (Sambrook, J. et al. (1989)).

RT-PCR—About 5 ug of total cellular RNA was isolated by extraction of lymphoblastoid cell lines or kidney tissues of VHL patients or 2.5 ng of normal adult kidney double-stranded complementary DNA samples were analyzed for expression using RT-PCR kit from Perkin-Elmer/Cetus. The primers were derived from the g7 cDNA sequence shown in SEQ. ID. NO: 1 and the reactions were run using various annealing temperatures. The reaction products were analyzed by gel electrophoresis and Southern blotting (Sambrook, J. et al (1989)).

Cell Culture—The 293 cells (Graham, et al. 1977) and UMRC 6 cells (Grossman, et al. 1995) were grown in DMEM medium supplemented with 10% fetal bovine serum (Life Technologies Inc., NY) penicillin (25 000 U/I) and streptomycin (25,000 $\mu g^{-1}$) with 8% $CO_2$.

Isolation of RNA for Identification of Promoter Region—Total RNA from cell cultures was isolated using Ultraspec II RNA isolation system (Biotex, TX). Poly(A)$^-$RNA was purified twice on oligo-dT Cellulose (Stratagene, CA).

RNAse H mapping—Ten micrograms of total RNA and 200 ng of VHL-specific antisense oligomer were annealed and RNA was digested with RNAse H essentially as described by Berger (1987). The following oligonucleotides were used; for VHL exon 1 (SEQ. ID. NO. 37): 5'-ACG ACG CGC GGA CTG CGA TTG CAG AAG AT-3': for exon 3 (SEQ. ID. NO. 38): 5'-AGC GAC CTG ACG ATG TCC AGT CTC-3'. After ethanol precipation, RNA was separated in 0.75 k agarose-formaldehyde gels (Lehrah, et al., 1977) transferred to nylon membrane and hybridized to the probe.

Mapping of the Transcription Start Site—Transcription start mapping was performed using Ribonuclease Protection Assay Kit (RPA II, Ambion, Tex.) according to manufacturer instructions. Protected fragments were separated in a standard urea sequencing gel (6% polyacrylamide). The gel was vacuum dried and exposed to X-ray film (Kodak X-OMAT AR). Sequencing ladder was made using control template, primer and reagents from Sequenase Version 2.0 DNA sequencing kit (United States Biochemical, OH).

RNA markers, probes and control sense VHL RNA were obtained by in vitro transcription using RNA Maxiscript T3/T7 kit (Ambion, Tex.) and three groups of templates. The first group (FIG. 8A, probes 1, 2, 3 and 4) derived from plasmid pBluescript II S/K (Stratagene, CA) carrying an inserted 892 bp EcoRI-NotI genomic fragment, containing the 5' part of VHL exon 1 and 5' flanking genomic region (−647/+245). For generation of probes no. 1, no. 2, no. 3 and no. 4 some parts of the insert were deleted and derivative plasmids were linearized as shown in FIG. 8A. The second group of templates was generated by PCR using the primers 5'-CCT CGC CTC CGT TAC AAC A-3' (SEQ. ID. NO. 39) and 5'-GGA TCC TAA TAC GAC TCA CTA TAG GGA GGC GCC CGA CTC CTC CC-3' (SEQ. ID. NO. 40). This PCR fragment contained part of the genomic EcoRI-NotI sequence (residues −166/+173) and the promoter of T7 RNA polymerase to make antisense VHL probe. To generate several marker probes, the template was cleaved around presumptive transcription start sites with EagI, BssHII, AluI or BamHI (FIG. 8A, probes 5, 6, 7 and 8). These probes were hybridized to probe no. 4 (control sense RNA) and the protected fragments were used as markers on FIG. 8C. The third set of templates (RNA Century Marker Template Set) was purchased from Ambion (Tex.). All templates were blunt ended with Klenow fragment.

Luciferase Plasmid Construction—Presumptive promoter region was amplified by PCR using upstream (sense) primer 5'-CTA TCT AGA GGC CAA GGC AGG AGG ATC-3' (SEQ. ID. NO. 41) and two downstream (antisense) primers: 5'-CAT TCT AGA TTC CCT CCG CGA TCC AGA-3' (SEQ. ID. NO. 42) and 5'-CAT TCT AGA CTC TTC CGG GCC GGA CTC-3' (SEQ. ID. NO. 43). The two PCR fragments contained residues 180–716 and 180–842 of the genomic EcoRI-NotI fragment (respectively residues −468− 69 and −468+195 on FIG. 12) and XbaI linkers. PCR fragments were digested with XbaI and cloned in both orientations into the NheI site of the pGL-2 enhancer vector (Promega, WI) . Series of 3' and 5' deletion constructs were generated using appropriate unique restrictases within the insert and in pGL-2 polylinker (MluI—for 5' deletions and BglII for 3' deletions). The plasmids carrying SV 40 early promoter (in pGL-2 control: Promega) and thymidine kinase promoter (in pTK, Gill, et al., 1994) were used as positive controls.

Transfection and Assays of Luciferase Activity −293 and UMRC 6 cells were transfected using the lipofectin protocol as described elsewhere (Chang and Brenner, 1988). For each 35mm plate 2$\mu$g of the luciferase reporter plasmid, 1 $\mu$g of pCMVβ (Clontech, CA) and 10l of Lipofectin (Gibco-BRL) were added. Luciferase and β-galactosidase assays were performed 40h after transfection using luciferase and β-galactosidase assay kits (Promega). The luciferase assay was performed using a Monolight 2010 luminometer (Analytical Luminescence Laboratory, CA).

Construction of the VHL Minigenes—Expression construct (pRc-HAVHL), which contained VHL reading frame subcloned into pRc CMV vector (Invitrogen, CA), was kindly provided by Dr. William G. Kaelin Jr. (Division of Neoplastic Disease Mechanisms, Dana Farber Cancer Institute, Harvard Medical School, Boston, Mass.). Group 7 VHL cDNA in pBluescript II KS was described elsewhere (Latif, et al., 1993), 1.4 kb NotI fragment from group 7 construct (exons 3, 2 and 3' part of exon 1) was inserted in correct orientation into NotI site of plasmid pNE (pBluescript II SK carrying VHL 5' flanking 892 bp EcoRI-NotI genomic fragment, including 5' part of exon 1). The final plasmid (pVHL) was used to generate three expression constructs in which VHL minigene was driven by its own promoter as follows: (1) pRcpVHL: after digestion of pRc-HAVHL with NruI-Baste, CMV promoter/enhancer and part of the VHL reading frame were removed and substituted by VHL promoter and exon 1 from pVHL (EcoRV-Baste digest); (2) pRcpVHLm: plasmid pRcpVHL was linearized with Baste, filled-in with Klenow fragment and religated: (3) pRcpVHL3U: Baste-XbaI fragment in pRcpVHL was substituted by Baste-XbaI fragment from pVHL, which contained additional 0.9 kb from 3' untranslated region.

Stable Transfection of the UMRC6 Cells—Eighty percent confluent UMRC 6 cells were transfected with 25 $\mu$g DNA and 40 pl of lipofectin in 5 ml OPTI-MEM medium (Life Technologies Inc., NY) per 100 mm plate for 12 h and grown in DMEM medium. In a day, 400 $\mu$g ml$^{-1}$ of active geneticin was added and resistant colonies were grown for 2 to 3 weeks. Selective media was changed every 3 days.

EXAMPLES

The Examples herein are meant to exemplify the various aspects of carrying out the invention and are not intended to limit the scope of the invention in any way.

EXAMPLE 1

Isolation of the VHL Disease Gene

Figure 1:
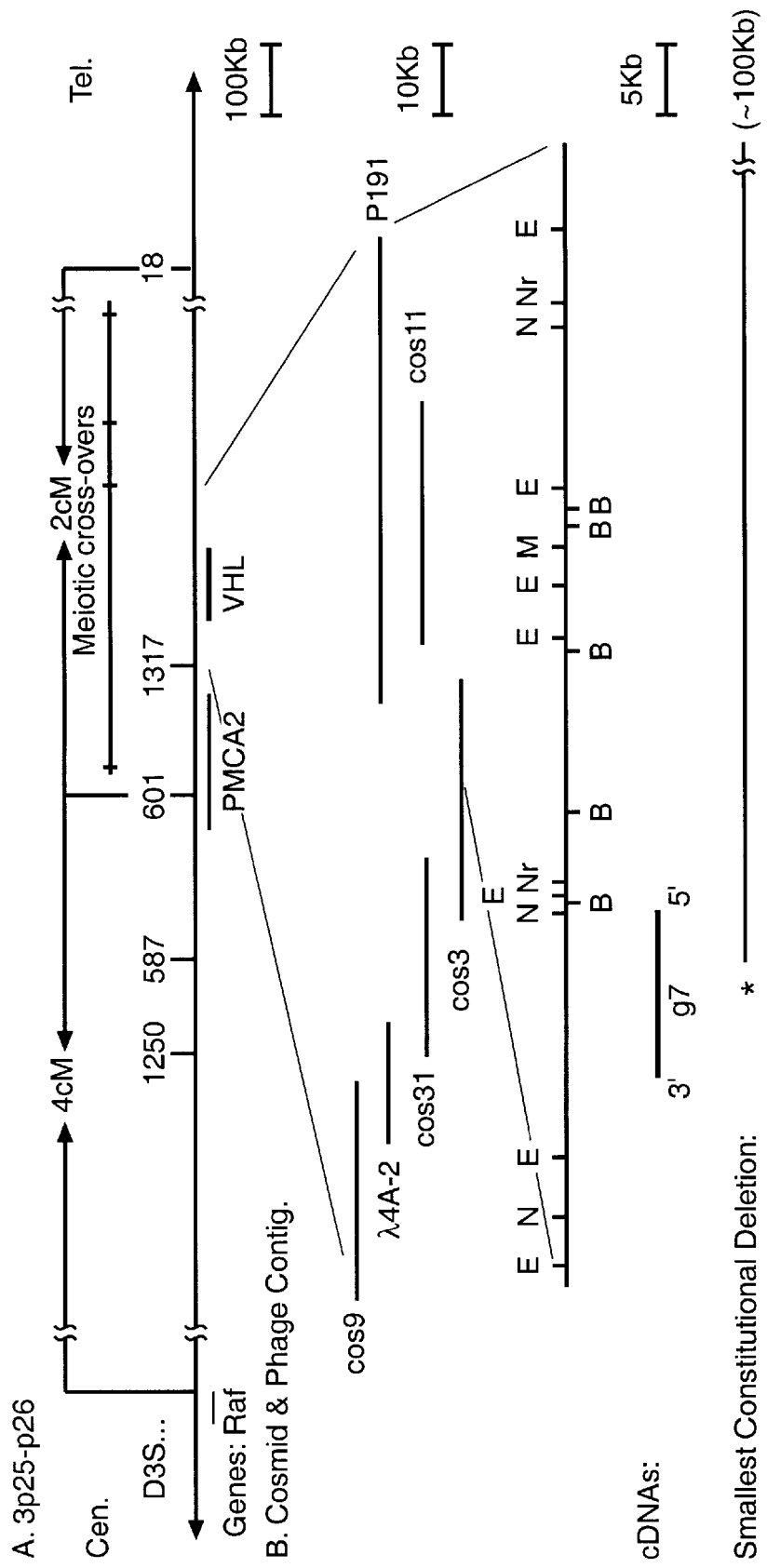
FIG. 1.

The isolation of the VHL disease gene resulted from the use of positional cloning strategies (Latif et al., Cancer Res. (1993) 63:861–867; Trofatter et al., Cell (1993) 72:791–800 and The Huntington's Disease Collaborative Research Group; Cell (1993) 72:971–983) previously used in isolating disease genes and is described in Latif, et al., *Science*, (1993) 260:1317–1320. Genetic and physical map of the chromosome 3p region encompassing the VHL gene is shown in FIG. 1. The VHL locus was positioned on the map (FIG. 1 Panel A) by multipoint linkage analysis and meiotic mapping (Tory et al., 1989); the location of selected cross-overs is indicated by crosses. YAC Library Screening and Analysis of YACs. Copies of the WU and CEPH YAC libraries were obtained from Dr. Craig Chinault (Baylor Institute of Human Genetics, Houston, Tex.) and Dr. Daniel Cohen, respectively (centre d'Etude du Polymorphisme Humain, Paris). The WU and CEPH libraries are total human genomic DNA libraries constructed in the PYAC4 vector (Burke, D. T. et al. Science (1987) 236:806–812; Anand, R. et al. Nucleic Acids Res. (1990) 18: 1951–1956). These libraries were screened by sib selection using PCR-based techniques (Greene, E. D. et al., Proc. Natl. Acad Sci. (1990) 87:1213–1217) with primers for the D3S601, D3S587 and D3S18 loci in the VHL region (FIG. 1). The sequences of the primers used to positively identify YACs Y52A10, YA101D4, Y132F2 and Y70D2 are shown below as SEQ. ID. NO. 44 thru SEQ. ID. NO. 49:

| Locus/Location | Designation | Sequence |
|---|---|---|
| D3S18/3p26 | ML-1 | CACAAGTGAT GCCTTGTAGC TG SEQ. ID. NO. 44 |
| D3S18/3p26 | ML-2 | CAGTAGTGTC CTGTATTTAG TG SEQ. ID. NO. 45 |
| D3S601/3p25.3 | ML-7 | GTTGGCTATG GGTAGAATTG G SEQ. ID. NO. 46 |
| p3S601/3p25.3 | ML-8 | CAGGGTAGCC TTGATCTAAG T SEQ. ID. NO. 47 |
| D3S587/3p25.2 | ML-10 | GGAGGTCCTG AGAATATGTG TCC SEQ. ID. NO. 48 |
| D3S587/3p25.2 | ML-11 | TGTTCAGGCA CACAGTAGAT G SEQ. ID. NO. 49 |

Screening Chromosome 3 Cosmid Library and Cosmid Contig Assembly. The chromosome 3 cosmid library was constructed as described in Lerman, et al. (Lerman, M. I. et al. Hum. Genet. (1991) 86:567–577). This library was screened by colony hybridization (Sambrook, J. et al. (1989)) using the YAC DNA inserts as probes as described in Baxendale, et al. (Baxendale, S. et al. Nucl. Acids Res. (1991) 19:6651). After labeling with $^{32}$P-dCTP, the probes were preassociated with a 1000×excess of sheared human DNA. Cosmid contigs were constructed by finding overlapping bands on Southern blots of EcoRI-digested cosmids using whole cosmids as probes. Gaps in the cosmid contigs were closed by chromosome walking using insert-end fragment probes, which were identified by restriction mapping and hybridization to restricted genomic DNA. These insert-end fragment probes were used for each walk step. FIG. 1 shows the 160 kb cosmid and phage contig covering the VHL region. The phage T42 was isolated by screening a total genomic phage library with YAC DNA inserts as described above. The phage pl91, which contains the VHL gene, was isolated by screening a three-hit P1 phage genomic library (Genome System, Inc. St. Louis, Mo.) with primers chosen from within an exon of the g7 cDNA sequence shown in SEQ ID NO. 1. The phage pl91 was deposited with the ATCC on May 13, 1993.

---

What is claimed is:

1. A method for detecting a mutant allele of a wild-tvDe VHL gene in a subiect suspected of having VHL disease or a disease related to the presence of a mutation in the wildtype VHL gene, said method comprising analyzing a nucleic acid sequence of a subject for the presence of said mutant allele, wherein said analyzing step is performed using a nucleic acid probe, and wherein said probe has a sequence consisting of or said probe has a sequence which is fully complementary to a full length sequence selected from the group consisting of SEQ ID NO: 7 through SEQ ID NO: 11, SEQ ID NO: 16, SEQ ID NO: 23 through SEQ ID NO: 28 and SEQ ID NO: 52 through SEQ ID NO: 53.

2. A method for detecting a mutant allele of a wild-type VHL gene in a subject suspected of having VHL disease or a disease related to the presence of a mutation in the wild-type VHL gene, said method comprising analyzing a nucleic acid sequence of a subject for the presence of said mutant allele, wherein said analyzing step is performed using at least one nucleic acid probe, and wherein said probe(s) is selected from the group consisting of (A) a probe consisting of at least 15 contiguous nucleotides of SEQ ID NO: 1 or complement thereof used in combination with a probe having any one of SEQ ID NO: 3 through 6, or complement thereof and (B) a probe having any one of SEQ ID NO: 3 through 6, or complement thereof.

3. The method of claim 2, wherein said probe has a sequence consisting of or said probe has a sequence which is fully complementary to a full length sequence selected from the group consisting of nucleotides 1–146, 169–391, 291–501, 585–940, 921–1231 and 1277–1600 of SEQ ID NO: 1.

4. The method of claim 1 or 2 wherein said step of analyzing comprises Southern blot analysis.

5. The method of claim 1 or 2 wherein said sequence is DNA.

6. A method for detecting a mutant allele of a wild-type VHL gene in a subiect suspected of having VHL disease or a disease related to the presence of a mutation in the wild-tyDe VHL gene, said method comprising analyzing a nucleic acid sequence of a subiect for the presence of said mutant allele, wherein said analyzing step is performed using nucleic acid primers, and wherein said primers have a nucleic acid sequence consisting of or a nucleic acid sequence full complementary to a full length sequence selected from the group consisting of SEQ ID NO: 7 through SEQ ID NO: 11, SEQ ID NO: 16, SEQ ID NO: 23 through SEQ ID NO: 28 and SEQ ID NO: 52 through SEQ ID NO: 53.

7. A method for detecting a mutant allele of a wild-type VHL gene in a subject suspected of having VHL disease or a disease related to the presence of a mutation in the wild-type VHL gene, said method comprising analyzing a nucleic acid sequence of a subject for the presence of said mutant allele, wherein said analyzing step is performed using nucleic acid primers, and wherein the primers are selected from the group consisting of (A) a primer consisting of at least 15 contiguous nucleotides of SEQ ID NO: 1 or complement thereof used in combination with a primer having any one of SEQ ID NO: 3 through 6, or complement thereof and (B) a primer having any one of SEQ ID NO: 3 through 6, or complement thereof.

8. The method of claim 7, wherein said primer has a sequence consisting of or a nucleic acid sequence fully complementary to a full length sequence selected from the group consisting of nucleotides 1–146, 169–391, 291–501, 585–940, 921–1231 and 1277–1600 of SEQ ID NO: 1.

9. A method of claim 6 or 7 wherein said step of analyzing is carried out by PCR-SSCP.

10. A method for detecting a mutant allele of a wild-type VHL gene in a subiect suspected of having VHL disease or a disease related to the presence of a mutation in the wild-type VHL gene, said method comprising analyzing a nucleic acid sequence of a subject for the presence of said mutant allele, wherein said analyzing step is performed using a nucleic acid probe or nucleic acid primers, and wherein said probe or primers have a nucleic acid sequence consisting of, or sequence fully complementary to a full length sequence selected from the group consisting of SEQ ID NO: 7 through SEQ ID NO: 11, SEQ ID NO: 16, SEQ ID NO: 23 through SEQ ID NO: 28 and SEQ ID NO: 52 through 53.

11. A method for detecting carriers of the VHL disease gene comprising: analyzing a nucleic acid sequence of a subject for mutations or alterations in a wild-type VHL nucleic acid sequence wherein the detection of said mutations or alterations identifies an individual as a carrier of the VHL disease gene, wherein said analyzing step is performed using at least one nucleic acid probe or nucleic acid primers, and wherein said probes or primers are selected from the group consisting of (A) a probe or primers consisting of at least 15 contiguous nucleotides of SEQ ID NO: 1 or complement thereof used in combination with a probe or primer having any one of SEQ ID NO: 3 through 6, or complement thereof and (B) a probe or primers having any one of SEQ ID NO: 3 through 6, or complement thereof.

12. The method of claim 11, wherein said probe or primer has a sequence, consisting of or full complementary to a fully length sequence selected from the group consisting of nucleotides 1–146, 169–391, 291–501, 585–940, 921–1231 and 1277–1600 of SEQ ID NO: 1.

13. The method of claim 10 or 11, wherein said step of analyzing comprises PCR.

14. Primers or probes having nucleic acid sequences consisting of, or nucleic acid sequences fully complementary to a full length sequence selected from the group consisting of SEQ ID NO: 7 through SEQ ID NO: 11, SEQ ID NO: 16, SEQ ID NO: 23 through SEQ ID NO: 28 and SEQ ID NO: 52 through SEQ ID NO: 53.

15. A composition comprising primers or probes selected from the group consisting of (A) primers or probes consisting of at least 15 contiguous nucleotides of SEQ ID NO: 1 or complement thereof and primers or probes having any of SEQ ID NO: 3 through SEQ ID NO: 6 or complement thereof, and (B) primers or probes having any one of SEQ ID NO: 3 or 6, or complement thereof.

16. The composition of claim 15, wherein said probe or primer has a sequence consisting of or a sequence fully complementary to a full length sequence selected from the group consisting of nucleotides 1–146,169–391, 291–501, 585–940, 921–1231 and 1277–1600 of SEQ ID NO: 1.

17. A diagnostic kit for use in detecting carriers or for use in detecting mutant alleles of a wild-type VHL gene, said kit consisting of primers or probes, wherein said primers or probes have nucleic acid sequences consisting of or said primers or probes have a sequence which is fully complementary to a full length sequence selected from the group consisting of SEQ ID NO: 7 through SEQ ID NO: 11, SEQ ID NO: 16, SEQ ID NO: 23 through SEQ ID NO: 28, and SEQ ID NO: 52 through SEQ ID NO: 53.

18. A diagnostic kit for use in detecting carriers or for use in detecting mutant alleles of a wild-type VHL gene, said kit comprising a composition of primers or probes, wherein said composition comprises (A) primers or probes consisting of at least 15 contiguous nucleotides of SEQ ID NO: 1 or complement thereof and primers or probes having any of SEQ ID NO: 3 through SEQ ID NO: 6 or complement thereof, or (B) primers or probes having any one of SEQ ID NO: 3 or 6, or complement thereof.

19. The kit of claim 18 wherein said primers or probes have a sequence consisting of or fully complementary to a full length sequence selected from the group consisting of nucleotides 1–146, 169–391, 291–501, 585–940, 921–1231 and 1277–1600 of SEQ ID NO: 1.

20. A method for detecting a mutant allele of a wild-type VHL gene in a subject suspected of having VHL disease or diseases related to the presence of a mutation in the wild-type VHL gene, said method comprising analyzing a nucleic acid sequence of a subject for the presence of said mutant allele, wherein said analyzing step is performed using a nucleic acid probe, and wherein said probe has a sequence consisting of, or said probe has a sequence which is fully complementary to a full length sequence selected from the group consisting of SEQ ID NO: 20, SEQ ID NO: 29 through 34, SEQ ID NO: 37 and SEQ ID NO: 38.

21. A method for detecting a mutant allele of a wild-type VHL gene in a subject suspected of having VHL disease or a disease related to the presence of a mutation in the wild-type VHL gene, said method comprising analyzing a nucleic acid sequence of a subject for the presence of said mutant allele, wherein said analyzing step is performed using nucleic acid primers, and wherein said primers have a nucleic acid sequence consisting of, or a nucleic acid sequence fully complementary to a full length sequence selected from the group consisting of SEQ ID NO: 20, SEQ ID NO: 29 through 34, SEQ ID NO: 37 and SEQ ID NO: 38.

22. A method for detecting carriers of the VHL disease gene comprising: analyzing a nucleic acid sequence of a subject for mutations of alterations in a wild-type VHL nucleic acid sequence wherein the detection of said mutations or alterations identifies an individual as a carrier of the VHL disease gene, wherein said analyzing step is performed using a nucleic acid probe or nucleic acid primers, and wherein said probe or primers have a nucleic acid sequence consisting of, or a nucleic acid sequence fully complementary to a full length sequence selected from the group consisting of SEQ ID NO: 20, SEQ ID NO: 29 through 34, SEQ ID NO: 37 and SEQ ID NO: 38.

23. Primers or probes having nucleic acid sequences consisting of, or a nucleic acid sequence fully complementary to a full length sequence selected from the group consisting of SEQ ID NO: 20, SEQ ID NO: 29 through 34, SEQ ID NO: 37 and SEQ ID NO: 38.

24. A diagnostic kit for use in detecting carriers or for use in detecting mutant alleles of a wild-type VHL gene, said kit comprising primers or probes, wherein said primers or probes have a nucleic acid sequence consisting of, or a nucleic acid sequence fully complementary to a full length sequence selected from the group consisting of SEQ ID NO: 20, SEQ ID NO: 29 through 34, SEQ ID NO: 37 and SEQ ID NO: 38.

* * * * *

UNITED STATES PATENT AND TRADEMARK OFFICE
CERTIFICATE OF CORRECTION

PATENT NO. : 6,312,890 B1
DATED : November 6, 2001
INVENTOR(S) : W. Marston Linehan, Michael I. Lerman, Farida Latif and Berton Zbar It is certified that error appears in the above-identified patent and that said Letters Patent is hereby corrected as shown below:

<u>Column 2,</u>
Line 67, the word "cosil" should read -- cos11 --.

<u>Column 9, line 42 through Column 18, line 64,</u>
Should be cut and inserted after Column 32, line 43.

<u>Column 12,</u>
Line 11, the term "3C-3C" should read -- 3C --.

<u>Column 26,</u>
Line 60, the word "calorimetric" should read -- colorimetric --

<u>Column 30,</u>
Line 49, the term "NruI-Baste" should read -- NruI-BstEII --;
Line 51, the term "EcoRV-Baste" should read -- EcoRV-BstEII --;
Line 53, the word "Baste" should read -- BstEII --;
Lines 54 and 55, the term "Baste-XbaI", each occurrence, should read -- BstEII-XbaI --;
Line 59, the term "pl" should read -- µl --.

<u>Column 61,</u>
Lines 29 and 67, the word "tvDe", each occurrence, should read -- type --.

<u>Column 63,</u>
Line 8, the word "probes" should read -- probe(s) --;
Line 11, the word "primer" should read -- primers --;

UNITED STATES PATENT AND TRADEMARK OFFICE
CERTIFICATE OF CORRECTION

PATENT NO.   : 6,312,890 B1
DATED        : November 6, 2001
INVENTOR(S)  : W. Marston Linehan, Michael I. Lerman, Farida Latif and Berton Zbar It is certified that error appears in the above-identified patent and that said Letters Patent is hereby corrected as shown below:

<u>Column 63 cont'd,</u>
Line 16, following the word "sequence," delete the comma;
Line 17, the word "fully" should read -- full --; and
Line 54, the words "any of" should read -- any one of --.

Signed and Sealed this

Twenty-fourth Day of December, 2002

JAMES E. ROGAN
*Director of the United States Patent and Trademark Office*